(12) United States Patent
Moss et al.

(10) Patent No.: US 8,044,057 B2
(45) Date of Patent: Oct. 25, 2011

(54) METHODS FOR SUPPRESSING AN IMMUNE RESPONSE OR TREATING A PROLIFERATIVE DISORDER

(75) Inventors: Joel Moss, Bethesda, MD (US); Arnold Kristof, Montreal (CA)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1496 days.

(21) Appl. No.: 10/581,257

(22) PCT Filed: Dec. 9, 2004

(86) PCT No.: PCT/US2004/041265
§ 371 (c)(1),
(2), (4) Date: May 30, 2006

(87) PCT Pub. No.: WO2005/056014
PCT Pub. Date: Jun. 23, 2005

(65) Prior Publication Data
US 2007/0173514 A1 Jul. 26, 2007

Related U.S. Application Data

(60) Provisional application No. 60/528,340, filed on Dec. 9, 2003.

(51) Int. Cl.
*A61K 31/496* (2006.01)
(52) U.S. Cl. .................................. 514/254.11
(58) Field of Classification Search .............. 514/254.11
See application file for complete search history.

(56) References Cited

U.S. PATENT DOCUMENTS

| 4,900,727 A | 2/1990 | Kattige et al. |
|---|---|---|
| 5,284,856 A | 2/1994 | Naik et al. |
| 5,703,075 A | 12/1997 | Gammill et al. |
| 2003/0050692 A1 | 3/2003 | Sirhan et al. |

FOREIGN PATENT DOCUMENTS
WO  WO 90/06921  6/1990

OTHER PUBLICATIONS

He et al., "Relationship Between Mesangial Cell Proliferation and Types I and IV Collagen mRNA Levels In Vitro," *Am. J. Physiol.*, 269 (Cell Physiol. 38): C554-C562, (1995).
International Search Report from parent PCT Application No. PCT/US2004/041265, 4 pp., (Apr. 19, 2005).
Rekhter and Gordon, "Cell Proliferation and Collagen Synthesis Are Two Independent Events in Human Atherosclerotic Plaques," *J. Vasc. Res.*, 31: 280-286, (1994).
Blume-Jensen and Hunter, "Oncogenic kinase signaling," *Nature* 411:355-365, May 17, 2001.
Brunn et al., "Direct inhibition of the signaling functions of the mammalian target of rapamycin by the phosphoinositide 3-kinase inhibitors, wortmannin and LY294002," *The EMBO Journal* 15(19):5256-5267, 1996.
Castedo et al., "Mammalian Target of Rapamycin (mTOR): Pro- and Anti-Apoptotic," *Cell Death and Differentiation* 2002 9:99-100, 2002.
Cohen, "Protein kinases—major drug targets of the twenty-first century?" *Nature Reviews* 1:309-315, Apr. 2002.
Dancey and Sausville, "Issues and Progress with Protein Kinase Inhibitors for Cancer Treatment," *Nature* 2:296-311, Apr. 2003.
Davies et al., "Specificity and mechanism of action of some commonly used protein kinase inhibitors," *Biochem. J.* 351:95-105, 2000.
Ding et al., "Antagonists of Phosphatidylinositol 3-Kinase Block Activation of Several Novel Protein Kinases in Neutrophils," *J. Biological Chemistry* 270(19):11684-11691, 1995.
El-Kholy et al., "The phosphatidylinositol 3-kinase inhibitor LY294002 potently blocks $K_v$ currents via a direct mechanism," *The FASEB Journal* 17:720-722, Apr. 2003.
Grünwald et al., "Inhibitors of mTOR Reverse Doxorubicin Resistance Conferred by PTEN Status in Prostate Cancer Cells," *Cancer Research* 62:6141-6145, Nov. 1, 2002.
Hu et al., "Inhibition of phosphatidylinositol 3'-kinase increases efficacy of paclitaxel in in vitro and in vivo ovarian cancer models," *Cancer Research* 62(4):1087-1092, Feb. 15, 2002.
Kozma and Thomas, "Regulation of cell size in growth, development and human disease: PI3K, PKB and S6K," *BioEssays* 24:65-71 (2002).
Majewski et al., "Immunosuppressive TOR Kinase Inhibitor Everolimus (RAD) Suppresses Growth of Cells Derived from Post-transplant Lymphoproliferative Disorder at Allograft-Protecting Doses," 75(10):1710-1717, May 27, 2003.

(Continued)

*Primary Examiner* — Jeffrey S. Lundgren
*Assistant Examiner* — Nelson Blakely, III
(74) *Attorney, Agent, or Firm* — Klarquist Sparkman, LLP

(57) ABSTRACT

Disclosed herein are methods for suppressing an immune response in a subject, treating a neoplasm in a subject, or treating a fibroproliferative vascular disease in a subject, that includes administering to the subject a therapeutically effective amount of a 2-(4-piperazinyl)-substituted 4H-1-benzopyran-4-one compound, or a pharmaceutically acceptable salt thereof, having the structure of Formula A

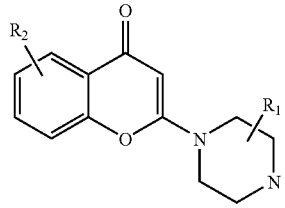

wherein the presence of each of $R_1$ and $R_2$ is optional and $R_1$ and $R_2$ are each independently selected from alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, halogen, hydroxy, or amino.

17 Claims, 11 Drawing Sheets

OTHER PUBLICATIONS

Raught et al., "The target of rapamycin (TOR) proteins," *PNAS* 98(13):7037-7044, Jun. 19, 2001.

Shegogue et al., "Collagen mRNA Stability is Regulated by mTOR vin a P13-Kinase Independent Pathway," *Molecular Biology of the Cell* 12(suppl):325a, Nov. 2001.

Vivanco et al., "The Phosphatidylinositol 3-Kinase-AKT Pathway in Human Cancer," *Nature Reviews* 2:489-501 (Jul. 2002).

Vlahos et al., "A Specific Inhibitor of Phosphatidylinositol 3-Kinase, 2-(4-Morpholinyl)-8-phenyl-4H-1-benzopyran-4-one (LY294002)," *J. Biological Chemistry* 269(7):5241-5248, Feb. 18, 1994.

"Novel method of immunosuppression," IRC Cyprus, Ref. 7918, Sep. 16, 2002, http://www.technology.org.cy/hephaestus/hephaestus.asp?det=yes&what=2324 printed Sep. 10, 2003, 1 page.

Mazzei et al., "*N,N*-Dialkylaminosubstituded Chromones and Isoxazoles as Potential Anti-inflammatory Agents," *IL Farmaco* 54:452-460 (1999).

Smith et al., "Functional Up-regulation of HERG $K^+$ Channels in Neoplastic Hematopoietic Cells," *The Journal of Biological Chemistry* 277 (21): 18528-18534 (May 24, 2002).

A

B

C

D

A

B

FIG. 7A
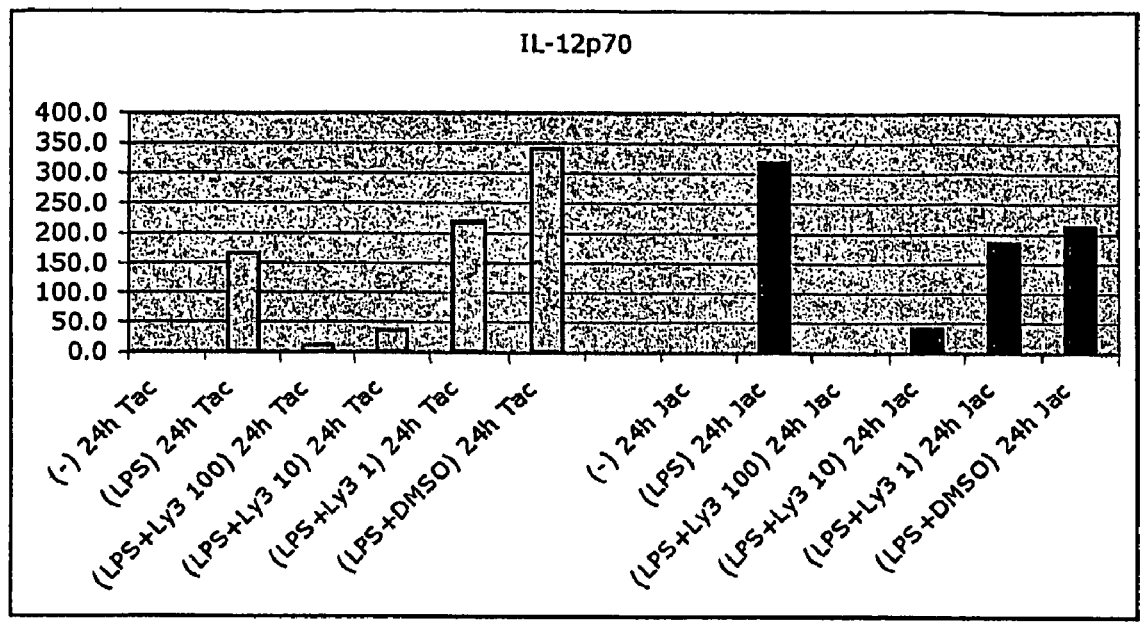
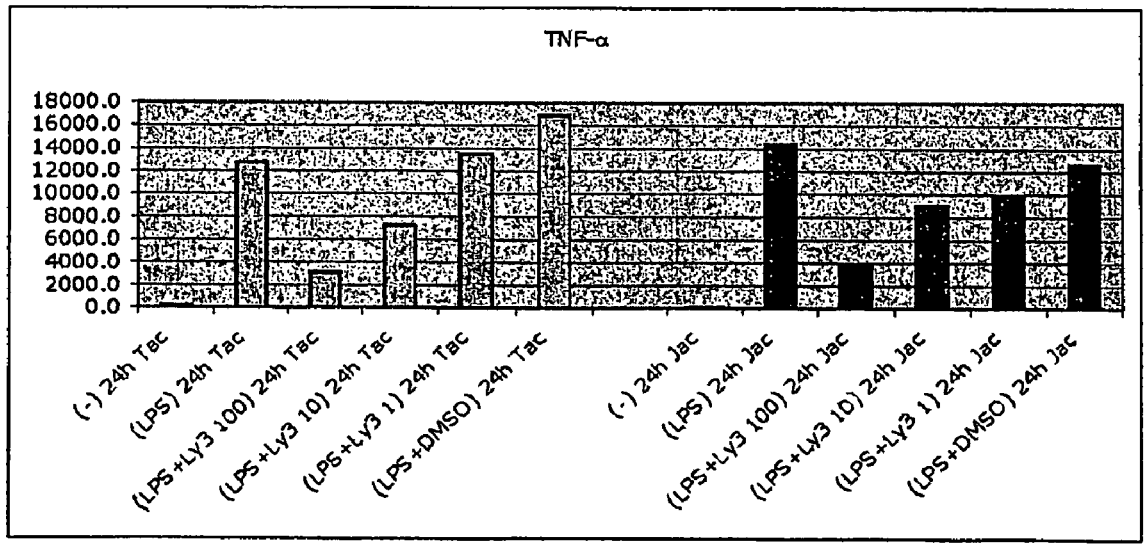
FIG. 7B

FIG. 7C
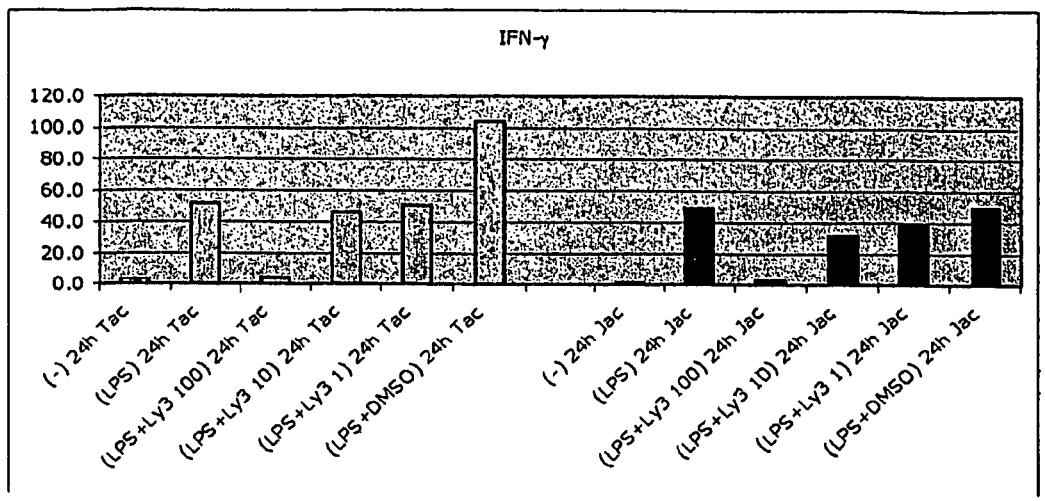
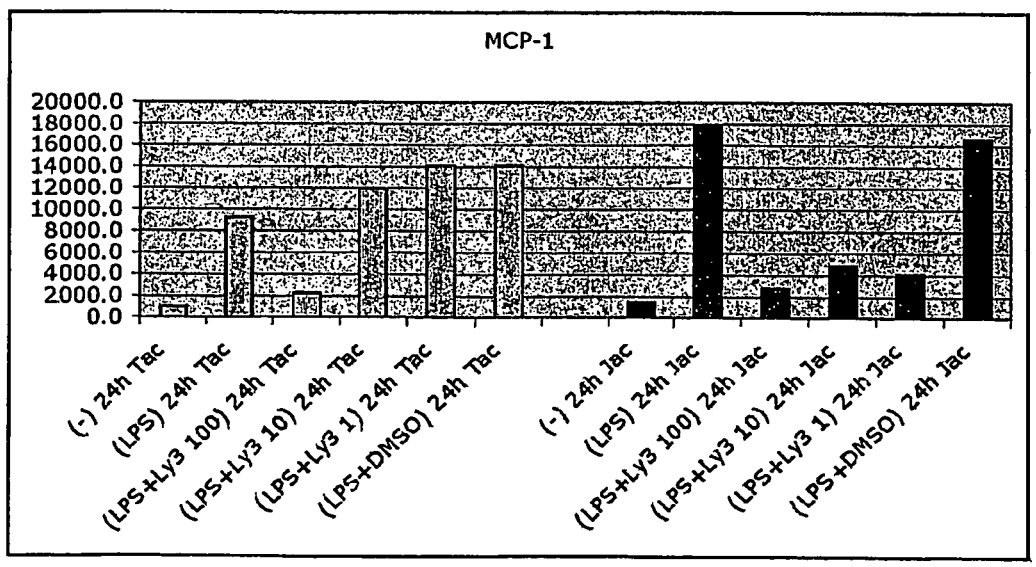
FIG. 7D

FIG. 7E
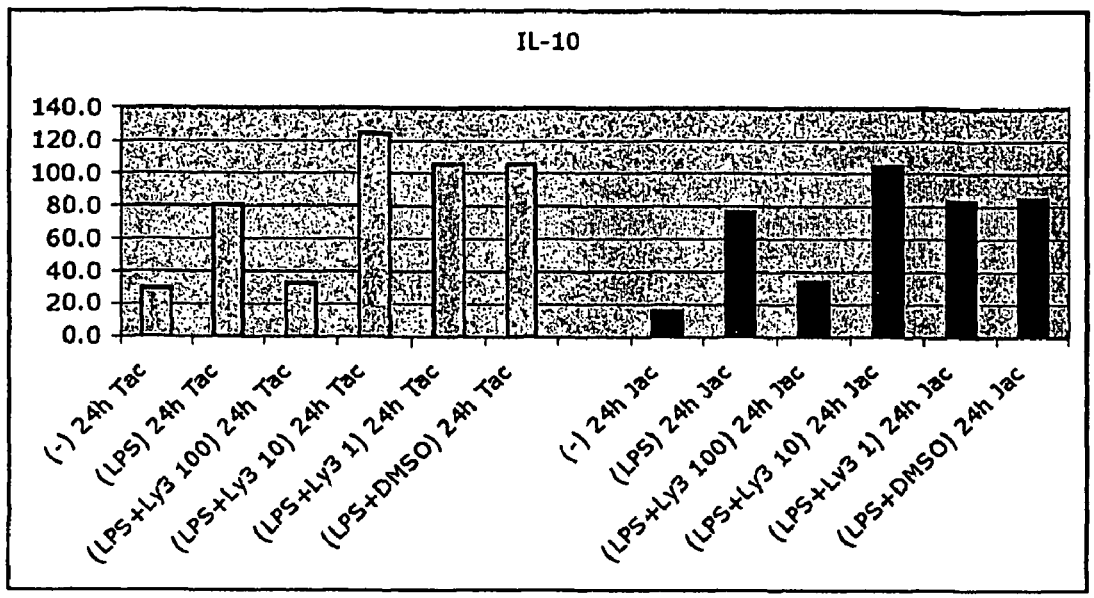
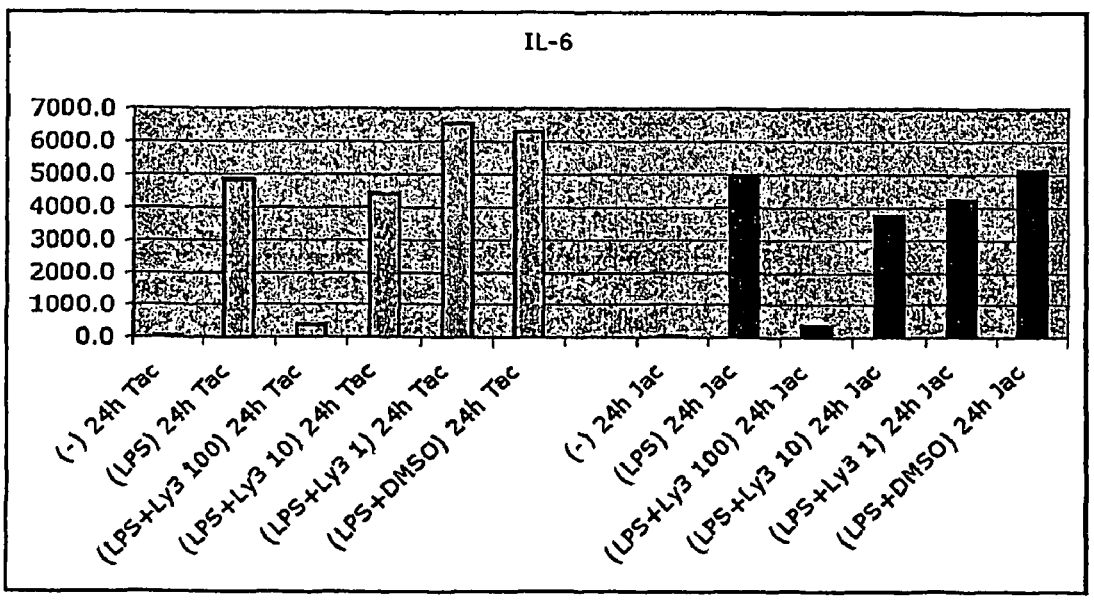
FIG. 7F

METHODS FOR SUPPRESSING AN IMMUNE RESPONSE OR TREATING A PROLIFERATIVE DISORDER

CROSS REFERENCE TO RELATED APPLICATIONS

This is a §371 U.S. national stage of PCT Application No. PCT/US2004/041265, filed Dec. 9, 2004, which was published in English under PCT Article 2(2), and claims the benefit of U.S. Provisional Application No. 60/528,340, filed Dec. 9, 2003, which is incorporated herein by reference.

FIELD

Disclosed herein are methods and pharmaceutical compositions for treating proliferative disorders and for suppressing an immune system response that involve administering certain 4H-1-benzopyran-4-one compounds to a subject.

BACKGROUND

Phosphatidylinositol 3-kinases (PI3K) phosphorylate phosphinositides at the 3-hydroxyl. These enzymes generate second messengers (for example, PIP3) and act as transducers downstream of tyrosine kinase receptors and G-protein coupled receptors. The PI3Ks are involved in a large number of fundamental processes including apoptosis, proliferation, cell motility, and adhesion. (see Walker et al., *Molec. Cell* 6:909-919, 2000). Thus, several PI3K inhibitors have been developed.

Mammalian Target of Rapamycin (mTOR) is a 289 kDa serine threonine kinase that is also known as FKBP-12 target-1 (RAFT-1) and FKBP-12 rapamycin associated protein. There are several conserved domains of mTOR, including a serine-threonine kinase domain. T cell models suggest that IL-2 and other factors promote mTOR activation and subsequently promote cell growth by inducing new protein synthesis. mTOR is known to contribute to the activation of P70 S6 kinases, which in turn catalyze phosphorylation of S6, a 40S ribosomal protein required for activating polysomes to drive protein synthesis and mRNA translation. In addition, mTOR activates the eukaryotic initiation factor 4E. Thus, mTOR plays a role in regulating protein synthesis and the cell cycle. It is believed that mTOR acts as a checkpoint by sensing cell status and regulating cell progress through the G1-S phase. Various known effector pathways upstream and downstream of mTOR are used to regulate mTOR activities. Thus, compounds that inactivate MTOR by binding to mTOR can be used to regulate cell cycle function, and thereby cell growth. As mTOR specifically functions in lymphocytes, inhibition of mTOR can also be used to alter signaling in T and B cells (see Kirken and Want, *Transplantation Proc.* 35:227S-230S, 2003).

Known mTOR inhibitors include LY294002 (2-(4-morpholinyl)-8-phenyl-4H-1-benzopyran-4-one) and rapamycin. Rapamycin is used in immunosuppression, chemotherapeutic protocols, and in the prevention of post-angioplasty coronary restenosis. LY294002 blocks PI3K-dependent phosphorylation of protein kinase B. Rapamycin has significant adverse effects, including hypercholesterolemia, drug-induced pheumonitis, renal toxicity, hypertension, and increasing the predisposition to opportunistic infections.

Undesired cell proliferation is a component of many disease processes. For example, undesired cell growth can lead to the formation of either benign or malignant tumors. According to the American Cancer Society, cancer is a group of diseases characterized by uncontrolled growth and spread of abnormal cells. If the spread is not controlled, it can result in death. Although cancer is often referred to as a single condition, it actually consists of more than 100 different diseases. These diseases are characterized by uncontrolled growth and spread of abnormal cells. Cancer can arise in many sites and behave differently depending on its organ of origin. There is a continued search for agents of use in the treatment of the different types of cancer.

Undesired cell growth is also a component of restenosis, the recurrence of stenosis or artery stricture after corrective surgery. Restenosis occurs after coronary artery bypass (CAB), endarterectomy, heart transplantation, and particularly after angioplasty, atherectomy, laser ablation or stenting. Restenosis is the result of injury to the blood vessel wall during the lumen opening procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat angioplasty or other procedure to alleviate the restenosis.

In an immune response, T and or B cells proliferate in response to a stimulus viewed as "exogenous" by the immune system. Although generally immune responses are beneficial, there are situations where a decreased immune response is desired. For example, in autoimmune disorders, the cells of the immune system incorrectly identify a self component as exogenous and proliferate in response to the self component. Inflammatory responses can be deleterious, as can immune responses against a transplanted organ.

There is clearly a need to develop agents that can reduce undesired cellular proliferation. These agents include agents that induce immunosuppression, chemotherapeutics, and agents for the treatment of restenosis.

SUMMARY

Disclosed herein are methods for suppressing an immune response in a subject and for treating a proliferative disorder in a subject. These methods include administering to the subject a therapeutically effective amount of a 2-(4-piperazinyl)-substituted 4H-1-benzopyran-4-one compound, or a pharmaceutically acceptable salt thereof, having the structure of

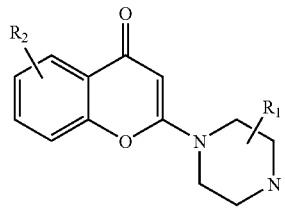

Formula A wherein the presence of each of $R_1$ and $R_2$ is optional and $R_1$ and $R_2$ are each independently selected from alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, halogen, hydroxy, or amino.

Also disclosed herein are methods for selecting an immunosuppressive agent or an anti-proliferative agent. The method includes selecting a test agent that preferentially inhibits casein kinase 2 and/or phosphorylation of P70 S6 kinase as compared to phosphatidylinositol 3-kinase (PI3K)-dependent phosphorylation of a substrate.

Further disclosed are pharmaceutical compositions comprising 2-(4-piperazinyl)-8-phenyl-4H-1-benzopyran-4-one or a pharmaceutically acceptable salt thereof, and a pharmaceutically acceptable carrier.

Cells were reacted with 0-100 µM LY303511 for 1 hour before addition of L/I for 30 min and preparation of cell lysates. Samples (70 µg) of proteins were separated by SDS-PAGE and transferred to nitrocellulose membranes before immunodetection of phospho-p70 S6 kinase T389 (pS6K), phospho-Akt S473 (pAkt), total p70 S6 kinase (S6K), total Akt (Akt), phospho-mTOR S2481 (pmTOR), or total mTOR (mTOR) by Western blot. Positions of protein standards (kDa) are on the right. For the bar graph and digital images shown in FIG. 1D, band density measurements were also represented graphically. Integrated band densities for pmTOR were normalized to those of total mTOR. Normalized band densities for cells treated with inhibitors are expressed relative to those treated with DMSO=1 (pmTOR/DMSO). Data are means of values from five experiments (±SEM). *$p<0.05$ by Student's t-test. All panels represent data from the same experiment, and are representative of four separate experiments.

Figure 2:
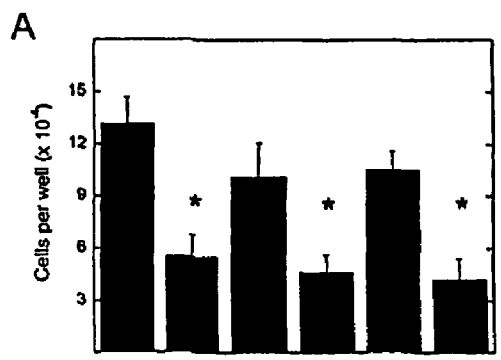
Figure 2:
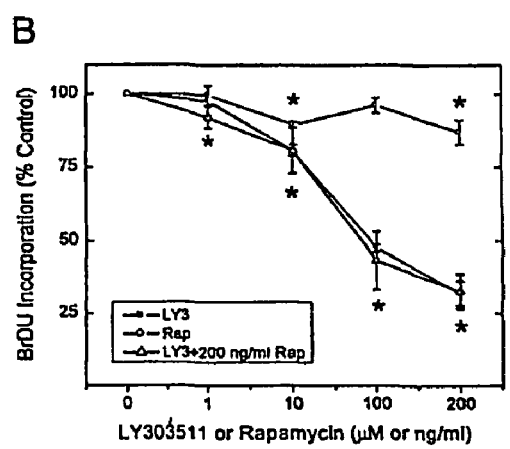
Figure 2:
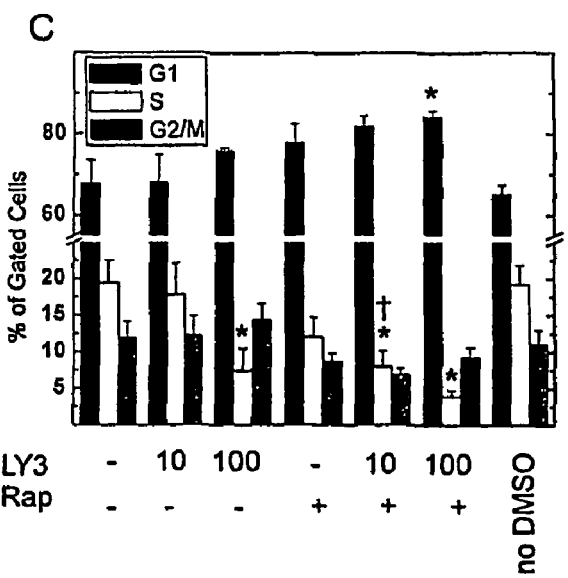

FIG. 2A is a bar graph showing LY303511 blocks cell proliferation, DNA synthesis, and cell cycle progression in A549 cells. A. A549 cells (80,000 cells per 35-mm dish) were grown for 1 day in medium with FBS before the addition of 0.1% DMSO, 100 µM LY303511, rapamycin, 200 ng/ml, 200 nM wortmannin, or 100 µM LY294002 for 24 hours. Cells were then incubated with trypsin, collected, and counted. Data are the means of cells/well×$10^{-4}$ ±SEM from duplicate assays in three experiments. *$p<0.05$ by Student's t-test. FIG. 2B is a line graph from results obtained when A549 cells (4,000 per well) in 96-well plates were grown in medium with FBS for 24 h before the addition of 10 mM BrDU plus 0-200 µM LY303511 without or with rapamycin, 200 ng/ml, or with rapamycin alone (0-200 ng/ml). BrDU incorporation (absorbance at 490/465) was measured by in situ ELISA as per the manufacturer's instructions (BrDU detection kit, Roche). For each experiment, BrDU in cells incubated with inhibitors was expressed as a percentage of that in cells treated with 0.2% DMSO control (% control). Mean absorbance measures for controls=100% in each experiment were 0.9±0.3, 0.8±0.3, and 0.8±0.3. Data are means of BrDU content ±SEM from triplicate assays in three experiments. *$p<0.05$ by Student's t-test. FIG. 2C is a bar graph showing LY303511 inhibits the cell cycle by combined G1 and G2/M arrest. A549 cells were grown in medium with FBS for 48 h before addition of 0-100 µM LY303511 without or with rapamycin, 200 ng/ml for 24 hours. Cells were then harvested and incubated with propidium iodide for 2 h before counting using a Becton-Dickson FACSCalibur. Data are means of percentages of cells in G1, S, or G2/M phase of the cell cycle ±SEM. *$p<0.05$ vs. DMSO control, or †$p=0.056$ vs. 10 µM LY303511, by Student's t-test.

Figure 3:
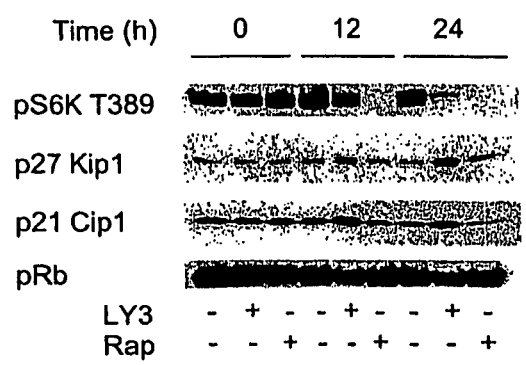
Figure 3:
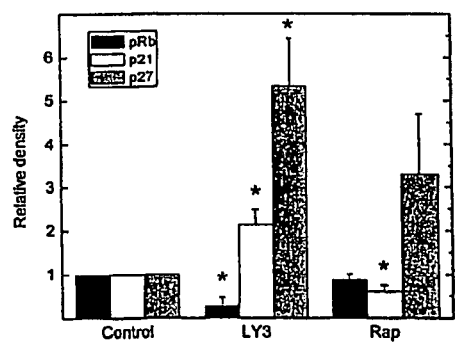
Figure 3:
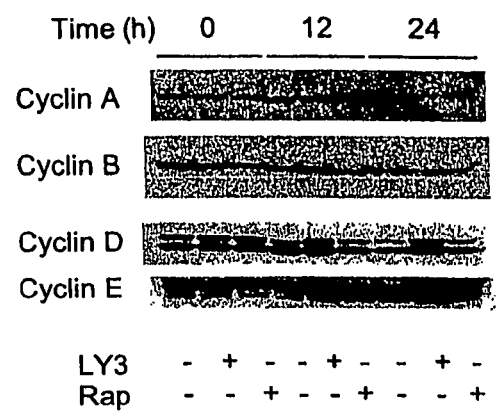
Figure 3:
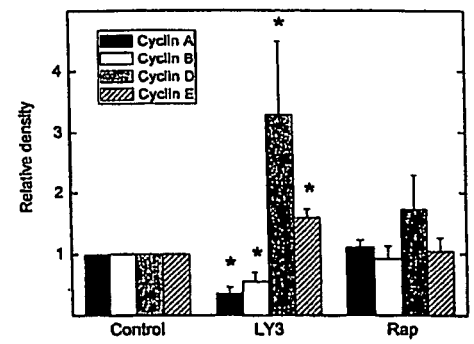

FIGS. 3A-3B are bar graphs and digital images showing the effect of LY303511 on the levels of cell cycle inhibitors and cyclins. A549 cells (~1×$10^6$ cells per 100-mm dish) were grown for 48 h before addition of 0.1% DMSO, 100 µM LY303511, or rapamycin, 200 ng/ml, for 0, 12, or 24 hours. At the indicated times, cells were homogenized and stored at −80° C. For Western blot analyses, samples (70 µg) of lysate proteins separated by SDS-PAGE were transferred to nitrocellulose membranes and reacted with the following antibodies: A. Phospho-S6K T389 (pS6K), p27 Kip1, p21 Cip1, phospho-Rb S807/S811, or B. Cyclin A, Cyclin B, Cyclin D, and Cyclin E. All blots are from one experiment. Data below (relative density) are means of densitometric values from duplicate dishes treated with inhibitors for 24 hours relative to DMSO control=1.0 in three experiments. *$p<0.05$ vs. DMSO control by Student's t-test.

Figure 4:
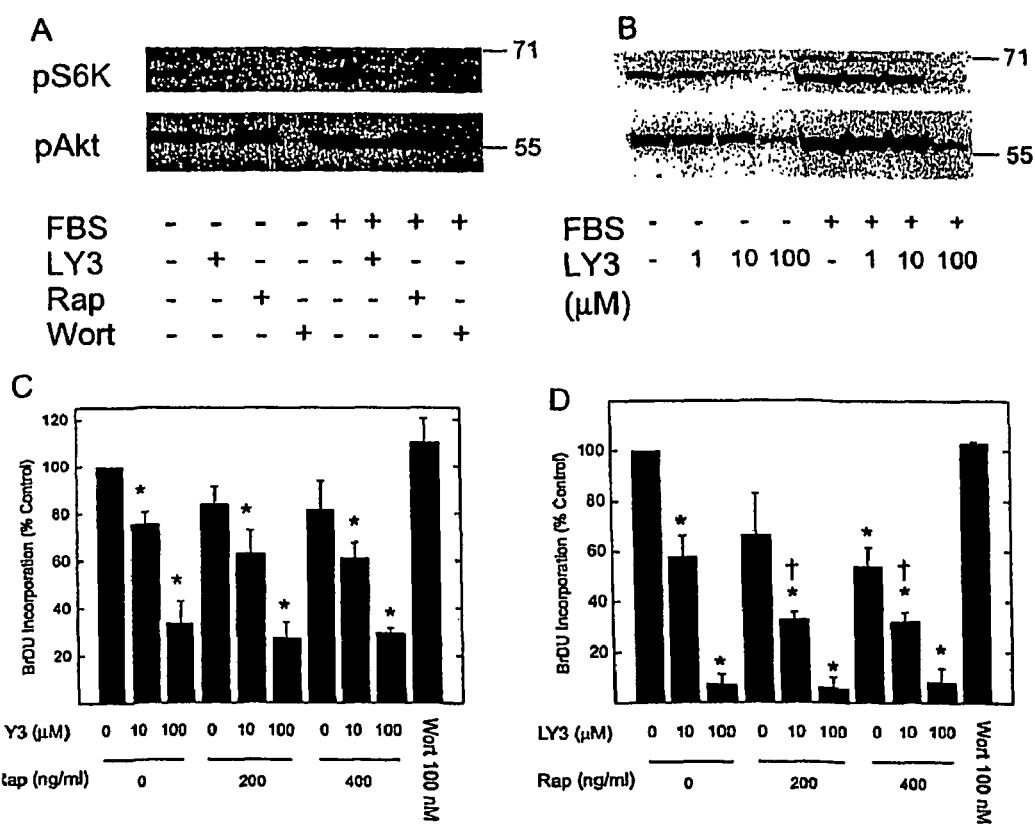

FIGS. 4A-4D are bar graphs and digital images showing that LY303511 inhibits serum-stimulated phosphorylation of S6K and Akt (FIGS. 4A and 4B), as well as proliferation in PASM cells (FIGS. 4C and 4D). After incubation in serum-free medium for 24 hours, PASM cells were incubated without or with 100 µM LY303511, rapamycin, 200 ng/ml, or 200 nM wortmannin (FIG. 4A), or 0-100 µM LY303511 (FIG. 4B), for 1 hour before the addition of 10% FBS for 30 min and preparation of cell lysates. Equal amounts of protein (20 µg/gel) were separated by SDS-PAGE and transferred to nitrocellulose membranes before immunodetection of phospho-p70 S6 kinase T389 (pS6K) or phospho-Akt S473 (pAkt) by Western blot. Data are from one experiment representative of five.

PASM cells (4,000 per well) were grown in 96-well plates for 24 hours before incubation for 24 hours in medium with (FIG. 4C) or without 10% FBS (FIG. 4D). Cells were then incubated in fresh medium containing 10% FBS, 10 µM BrDU, and 0-100 µM LY303511 without or with rapamycin, 200 or 400 ng/ml, for 24 hours BrDU incorporation was measured by in situ ELISA as per the manufacturer's instructions (BrDU detection kit, Roche). For each experiment, BrDU content of cells incubated with inhibitors was expressed relative to that in cells incubated with 0.1% DMSO control (% control). Mean control (=100%) absorbance for each experiment using cells from different donors was 0.22±0.06 and 0.24±0.06 for FIG. 4C and FIG. 4D, respectively (=100%). Data are means of BrDU values ±SEM from 3 experiments with assays in sextuplet. *$p<0.05$ vs. DMSO control, or †$p<0.05$ vs. 10 µM LY303511, by Student's t-test.

Figure 5:
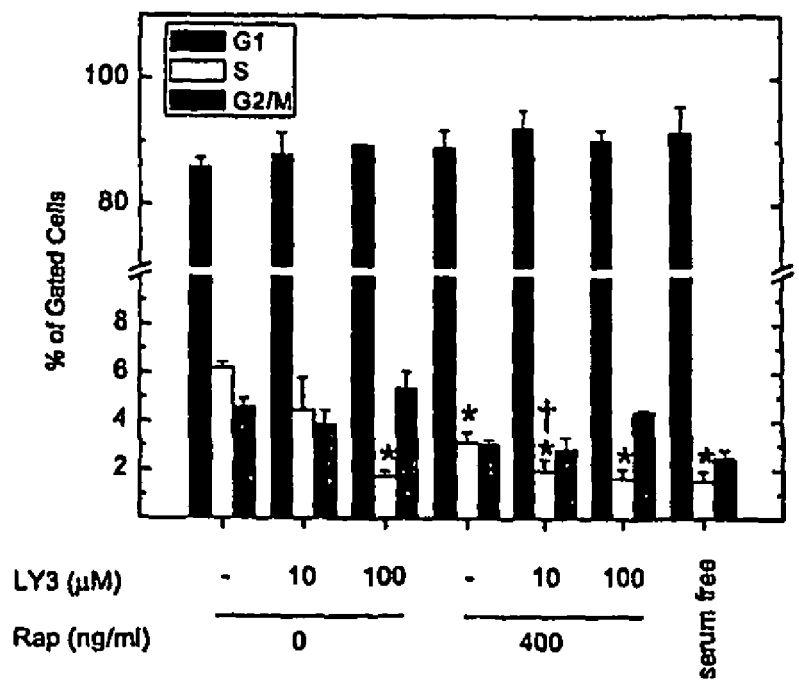
Figure 5:
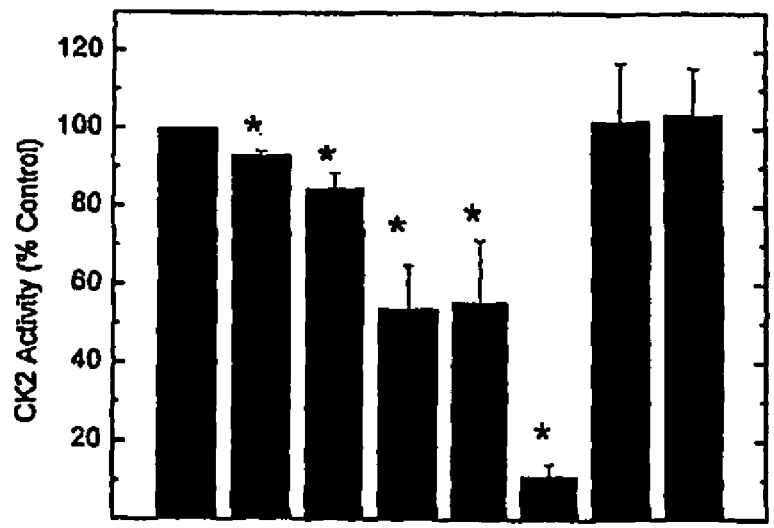

FIGS. 5A-5B are bar graphs showing that LY303511 inhibits the cell cycle by causing combined G1 and G2/M arrest and that LY303511 inhibits CK2 activity. For the data shown in FIG. 5A, PASM cells were cultured in medium with FBS for 48 hours before the addition of 0-100 µM LY303511 without or with raparnycin, 400 ng/ml, for 24 hours. Cells were then harvested and incubated with propidium iodide for 2 hours before counting using a Becton-Dickson FACSCalibur. Data are the means (±SEM) of percentages of cells in G1, S, or G2/M phase of the cell cycle in three experiments with duplicate assays. *$p<0.05$ vs. DMSO control, or †$p<0.05$ vs. 10 µM LY303511, by Student's t—test. FIG. 5B is a bar graph showing that LY303511 or LY294002 inhibits CK2 in vitro. As per the manufacturer (Upstate Biotechnologies), 0 or 100 ng of recombinant CK2 were incubated with CK2 substrate peptide and $^{32}$P-γ-ATP for 10 min with 1% DMSO or inhibitors as indicated. Data are the means of values for samples with inhibitors expressed as percentage of that for control, which was (mean±SEM) 0.2±0.03 pmol phosphate/100 ng protein/10 min. Data are from three experiments performed in duplicate. *p<0.05 by Student's t-test when compared to DMSO control.

Figure 6:
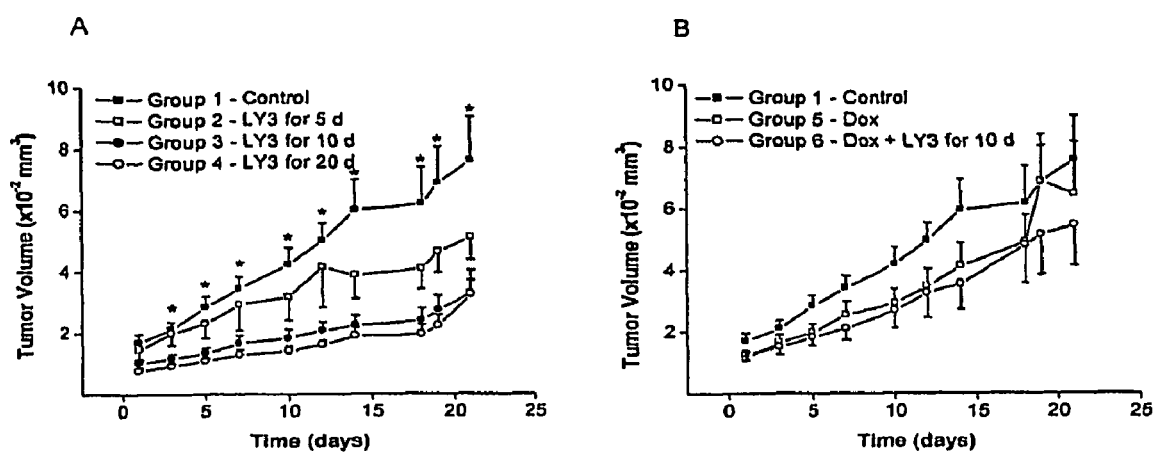
Figure 6C:
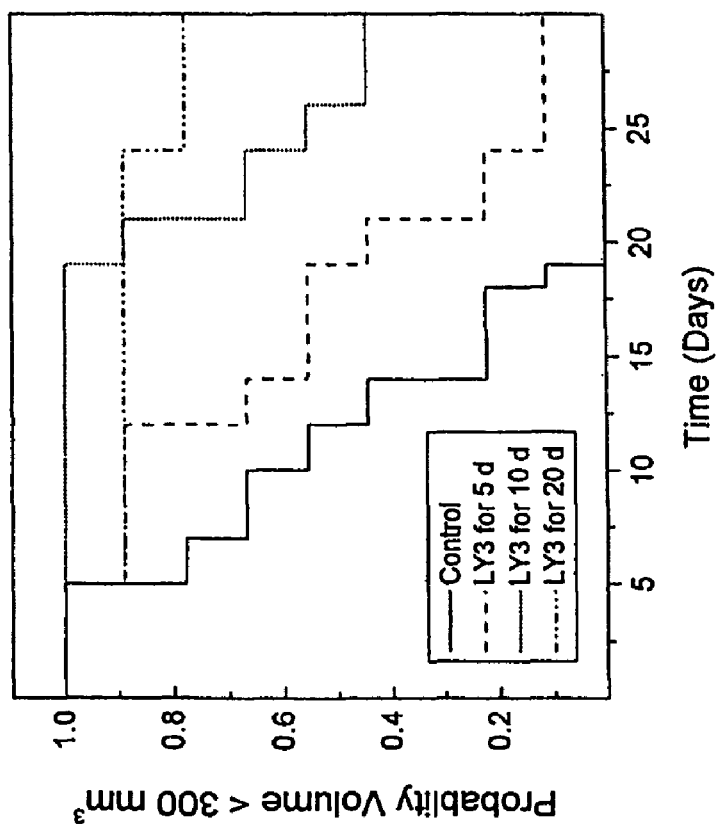

FIG. 6A-6B are bar graphs showing that LY303511 inhibits the growth of prostate adenocarcinoma cells (PC-3) cells in nude mice. LY303511, 10 mg/kg/d was administered intraperitoneally to attenuate PC-3 tumor growth in nude mice. The degree of growth inhibition was proportional to the duration of treatment with LY303511. A 20 day course of LY303511 (LY3) was as effective at inhibiting tumor growth as a ten day course. FIG. 6C is a graph of a Kaplan-Mieir survival analysis. The analysis includes the premise that an event happens when a tumor reaches 300 $mm^3$. The y-axis depicts the probability that tumor size is less than 300 $mm^3$. It should be noted that Group 4 had an early event, which likely represents an outlier (for example, the complete dose of drug may not have been received by the animal).

FIG. 7A-F are bar graphs showing that LY303511 inhibits lipopolysaccharide (LPS)—induced cytokine production or STAT1 activity in primary mouse peritoneal macrophages or A549 cells. Wild-type mice from Jackson (Jac) and Taconic (Tac) were used. Peritoneal macrophages were harvested three days after thioglycolate injection. Cells were incubated for three days in 2% FCS RPMI. The supernatant was collected after stimulation with LPS 1 μg/ml with or without LY 303511 (1~100 μM) or DMSO for 24 hours. Cytokines (interleukin (IL)-12p70, tumor necrosis factor (TNF)-α, interferon (IFN)-γ, MCP-1, IL-10, IL-6) were measured in cell supernatants. The results demonstrated that LY303511 caused a dose-dependent reduction of all six cytokines (see FIG. 7A-F). Addition of 100 μM LY303511 resulted in cytokine secretion similar to background levels. Thus, LY303511 clearly can reduce cytokine expression, and has an anti-inflammatory effect.

FIG. 8A-B are a set of bar graphs that shows inhibition of LPS/IFN-γ-induced STAT1 activity by LY303511. A549 cells were transiently transfected with a reporter vector expressing firefly luciferase driven by STAT1 (GAS-luc, Clontech), and incubated without or with 100 mcM LY303511, rapamycin, 200 ng/ml, or both, for 1 hour before addition of LPS/IFN-γ for 6 hours. STAT1 activity (luciferase activity) was measured in cell lysates (RLU). The data presented are triplicate samples ±SEM, and are representative of two independent experiments. As shown in FIGS. 4A and 4B, LY303511 inhibited STAT1 activation by two inflammatory mediators, LPS/IFN-γ.

DETAILED DESCRIPTION OF SEVERAL EXAMPLES

For ease of understanding, the following terms used herein are described below in more detail:

Chemical Terms

"Alkyl" refers to a cyclic, branched, or straight chain alkyl group containing only carbon and hydrogen, and unless otherwise mentioned typically contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents as described below.

"Substituted alkyl" refers to an alkyl as described above in which one or more hydrogen or carbon atom of the alkyl is replaced by another group such as a halogen, aryl, substituted aryl, cycloalkyl, substituted cycloalkyl, and combinations thereof. Illustrative substituted alkyls include benzyl, trichloromethyl, and the like.

"Heteroalkyl" refers to an alkyl as described above in which one or more hydrogen or carbon atom of the alkyl is replaced by a heteroatom such as N, O, P, B or S. An alkyl substituted with a heterocycloalkyl, substituted heterocycloalkyl, heteroaryl, substituted heteroaryl, alkoxy, aryloxy or amino is included within "heteroalkyl." Illustrative heteroalkyls include cyano, benzoyl, 2-pyridyl, 2-furyl and the like.

"Cycloalkyl" refers to a saturated or unsaturated cyclic non-aromatic hydrocarbon radical having a single ring or multiple condensed rings. Illustrative cycloalkyls include cyclopentyl, cyclohexyl, bicyclooctyl and the like.

"Substituted cycloalkyl" refers to cycloalkyl as described above in which one or more hydrogen or carbon atom is replaced by another group such as a halogen, aryl, substituted aryl, alkoxy, aryloxy, amino and combinations thereof.

"Heterocycloalkyl" refers to a cycloalkyl radical as described above in which one or more of the carbon atoms of the cyclic radical is replaced by a heteroatom such as N, O, P, B or S. Illustrative hetercycloalkyls include, for example, piperazinyl, morpholinyl, tetrahydropyranyl, tetrahydrofuranyl, piperidinyl, pyrrolindinyl, oxazolinyl and the like.

"Substituted heterocycloalkyl" refers to a heterocycloalkyl radical as described above in which one or more hydrogen or carbon atom is replaced by another group such as a halogen, aryl, substituted aryl, alkoxy, aryloxy, amino and combinations thereof.

"Aryl" refers to an aromatic substituent that may be a single aromatic ring or multiple aromatic rings that are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular examples, aryls have between 1 and 20 carbon atoms.

"Substituted aryl" refers to an aryl radical as described above in which one or more hydrogen or carbon atom is replaced by one or more functional groups such as alkyl, substituted alkyl, cycloalkyl, substituted cycloalkyl, heterocycloalkyl, substituted heterocycloalkyl, halogen, alkylhalos, hydroxy, amino, alkoxy, and thio. Illustrative substituted aryls include chlorophenyl, 3,5-dimethylphenyl, 2,6-diisopropylphenyl and the like.

"Heteroaryl" refers to aromatic rings in which one or more carbon atoms of the aromatic ring(s) are replaced by a heteroatom(s) such as N, O, P, B or S. Heteroaryl refers to structures that may be a single aromatic ring, multiple aromatic rings or one or more aromatic rings coupled to one or more nonaromatic rings. Illustrative heteroaryls include, for example, thiophene, pyridine, isoxazole, phthalidimide, pyrazole, indole, furan and the like.

"Substituted heteroaryl" refers to a heteroaryl radical as described above in which one or more hydrogen or carbon atom is replaced by one or more functional groups such as alkyl, substituted alkyl, cycloalkyl, substituted cycloalkyl, heterocycloalkyl, substituted heterocycloalkyl, halogen, alkylhalos, hydroxy, amino, alkoxy, and thio.

"Alkoxy" refers to an —OZ radical wherein Z is selected from alkyl, substituted alkyl, cycloalkyl, substituted cycloalkyl, heterocycloalkyl, substituted heterocycloalkyl, and combinations thereof. Illustrative alkoxy radicals include methoxy, ethoxy, benzyloxy, and t-butoxy. A related term is "aryloxy" wherein Z is selected from aryl, substituted aryl, heteroaryl, substituted heteroaryl, and combinations thereof.

Illustrative alkoxy radicals include phenoxy, substituted phenoxy, 2-pyridinoxy, 8-quinalinoxy and the like.

"Amino" refers to the group —$NZ^1Z^2$ wherein each of $Z^1$ and $Z^2$ is independently selected from hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, and combinations thereof.

"Thio" refers to the group —$SZ^1Z^2$ wherein each of $Z^1$ and $Z^2$ is independently selected from hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, and combinations thereof.

"Halogen" refers to fluoro, bromo, chloro and iodo substituents.

"Pharmaceutically acceptable salts" of the presently disclosed compounds include those formed from cations such as sodium, potassium, aluminum, calcium, lithium, magnesium, zinc, and from bases such as ammonia, ethylenediamine, N-methyl-glutamine, lysine, arginine, omithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification rnay alternatively be administered as a pharmaceutically acceptable salt thereof. "Pharmaceutically acceptable salts" are also inclusive of the free acid, base, and zwitterionic forms. Description of suitable pharmaceutically acceptable salts can be found in *Handbook of Pharmaceutical Salts, Properties, Selection and Use*, Wiley VCH (2002).

A "pharmaceutical agent" or "drug" refers to a chemical compound or composition capable of inducing a desired therapeutic or prophylactic effect when properly administered to a subject.

Other Terms

"AKT" refers to a serine/threonine protein kinase that has been shown to regulate cell survival signals in response to growth factors, cytokines, and oncogenic Ras. AKT becomes activated via the phosphoinositide-3-OH kinase (PI3K) pathway and by other upstream kinases. AKT inhibits cell death pathways by directly phosphorylating and inactivating proteins involved in apoptosis, including Bad, procaspase 9, and members of the Forkhead transcription factor family. AKT is also known as protein kinase B (PKB, GenBank Accession No. NP_005154).

An "animal" is a living multicellular vertebrate organism, a category that includes, for example, mammals and birds. A "mammal" includes both human and non-human mammals. "Subject" includes both human and animal subjects.

An "anti-proliferative agent" refers to an agent that decreases proliferation, or causes the death of cells. Anti-proliferative agents include chemotherapeutic agents.

"Atherosclerosis" refers to the progressive narrowing and hardening of a blood vessel over time. Atherosclerosis is a common form of ateriosclerosis in which deposits of yellowish plaques (atheromas) containing cholesterol, lipoid material, and lipophages are formed within the intima and inner media of large and medium-sized arteries.

An "autoimmune disease" is a disease in which the immune system produces an immune response (e.g., a B cell or a T cell response) against an antigen that is part of the normal host (i.e., an autoantigen), with consequent injury to tissues. An autoantigen may be derived from a host cell, or may be derived from a commensal organism such as the micro-organisms (known as commensal organisms) that normally colonize mucosal surfaces.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (e.g., Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like.

"Chemotherapy" refers to the administration of one or a combination of compounds, referred to as "chemotherapeutic agents" to kill or slow the reproduction of rapidly multiplying cells. Chemotherapeutic agents include those known by those skilled in the art, including but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol. Rapamycin has also been used as a chemotherapeutic.

"Graft-versus-host disease" refers to a complication of bone marrow transplants in which T cells in the donor bone marrow graft go on the offensive and attack the host's tissues. Graft-versus-host disease (GVHD) is seen most often in cases where the blood marrow donor is unrelated to the patient or when the donor is related to the patient but is not a perfect match. There are two forms of GVHD: an early form called acute GVHD that occurs soon after the transplant when the white cells are on the rise, and a late form called chronic GVHD.

Acute GVHD typically occurs within the first three months after a transplant and can affect the skin, liver, stomach, and/or intestines. The earliest sign is usually a rash on the hand, feet and face which may spread and look like sunburn. Severe problems with acute GVHD may include blisters on the skin, watery or bloody diarrhea with cramping, and jaundice (yellowing of the skin and eyes) reflecting liver involvement.

Chronic GVHD typically occurs 2-3 months after the transplant and causes symptoms similar to those of autoimmune disorders such as lupus and scleroderma. Patients develop a dry, itchy rash which is raised and like alligator skin. There also may be hair loss, decrease in sweating in the skin, and premature graying of the hair. Mouth dryness is a common symptom. It may progress to food sensitivity and spicy and acid foods may sting. The eyes may also be involved with dryness and feel irritated and become red. Almost any organ can be affected by chronic GVHD.

An "immune response" refers to response of a cell of the immune system, such as a B cell, a T cell, macrophage or polymorphonucleocyte, to a stimulus. An immune response can include any cell of the body involved in a host defense response, for example, an epithelial cell that secretes a cytokine. Cytokines include, but are not limited to interleukins (such as IL-12 (see Quesniaux, Research Immunology 143: 385-400, 1992), tumor necrosis factor (TNF)-α (see Aggarwal and Vilcek (eds) "Tumor necrosis factor: structure, function, and mechanism of action," Marcel Dekker Inc. 1992), interferon (IFN)-γ (see Farrar and Schreiber, *Ann. Rev. of Immunol.* 11: 571-611, 1993), monocyte chemoattractant protein (MCP)-1 (see Yoshimura and Leonard Cytokines 4: 131-52, 1992), IL-10 (see Zlotnik and Moore, *Cytokines* 3: 366-71, 1991), and IL-6 (see Van Snick, *Ann. Rev. Immunol.* 8: 253-78, 1990). It should be noted that descriptions of cytokines including their protein sequences, sequences of nucleic acids and descriptions of their functions are available on the internet, such as on the COPE: Cytokines Online Pathfinder Encyclopaedia website. An immune response (for example innate, adaptive) includes, but is not limited to, a response to an infection with a virus or a bacteria, an innate immune response, a response to a self antigen, or inflammation.

"Inununosuppression" refers to nonspecific unresponsiveness of cellular and/or humoral immunity. Immunosuppression refers to the prevention or diminution of an immune response and occurs when T and/or B cells are depleted in number or suppressed in their reactivity, expansion or differentiation. Immunosuppression may arise from activation of specific or non-specific T cells, such as $T_{reg}$ cells, from cytokine signaling, in response to irradiation, or by drugs that have generalized immunosuppressive effects on T and B cells.

An "immunosuppressive agent" refers to a molecule, such as a chemical compound, small molecule, steroid, nucleic acid molecule, or other biological agent, that can decrease an immune response such as an inflammatory reaction. Immunosuppressive agents include, but are not limited to an agent of use in treating arthritis (anti-arthritis agent). Specific, non-limiting examples of immunosuppressive agents are non-steroidal anti-inflammatory agents, cyclosporine A, FK506, and anti-CD4. In additional examples, the agent is a biological response modifier, such as Kineret® (anakinra), Enbrel® (etanercept), or Remicade® (infliximab), a disease-modifying antirheumatic drug (DMARD), such as Arava® (leflunomide), a nonsteroidal anti-inflammatory drug (NSAIDs), specifically a Cyclo-Oxygenase-2 (COX-2) inhibitor, such as Celebrex® (celecoxib) and Vioxx® (rofecoxib), or another product, such as Hyalgan® (hyaluronan) and Synvisc® (hylan G-F20). Rapamycin is an additional example of an immunosuppressive agent.

"Inflammation" or an "inflammatory process" refers to a complex series of events, including dilatation of arterioles, capillaries and venules, with increased permeability and blood flow, exudation of fluids, including plasma proteins and leukocyte migration into the inflammatory focus. Inflammation may be measured by many methods well known in the art, such as the number of leukocytes, the number of polymorphonuclear neutrophils (PMN), a measure of the degree of PMN activation, such as luminal enhanced-chemiluminescence, or a measure of the amount of cytokines present.

"Inhibiting" or "treating" a disease refers to inhibiting the full development of a disease or condition, for example, in a subject who is at risk for a disease such as an autoimmune disease, graft-versus-host disease, or rejection of a transplanted tissue or organ. "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

A "kinase" refers to an enzyme that catalyzes the transfer of a phosphate group from one molecule to another. A "serine threonine kinase" transfers phosphate groups to a hydroxyl group of serine and/or threonine in a polypeptide. "P70 S6 kinase" is a kinase that phosphorylates the S6 protein of the 40S subunit (small subunit) of ribosomes. GenBank Accession No. JE0377 sets forth an exemplary amino acid sequence of human P70 S6 kinase. A "phosphatidyl inositol 3-kinase" refers to an enzyme that phosphorylates inositol lipids at the D-3 position of the inositol ring to generate the 3-phosphoinositides, phosphatidylinositol 3-phosphate [PtdIns(3)P], phosphatidylinositol 3,4-bisphosphate [PtdIns(3,4)P$_2$] and phosphatidylinositol 3,4,5-trisphosphate [PtdIns(3,4,5)P$_3$]. GenBank Accession No. AAB53966 sets forth an exemplary amino acid sequence of the catalytic subunit of human phosphatidyl inositol 3-kinase. "Casein kinase 2" (GenBank Accession No. NP_001887) refers to an enzyme that preferentially phosphorylates acidic proteins such as caseins. GenBank Accession No. NP_001887 sets forth an exemplary amino acid sequence of casein kinase 2. Examples of casein kinase 2 substrates include p53 (GenBank Accession No. CAA25652), BH3 interacting domain death agonist (Bid; Accession numbers for alternative transcripts NP_001187.1, NP_932070.1, NP_932071.1),DNA Topoisomerase II (NP_001058). A "preferential" inhibition of a kinase refers to decreasing activity of one kinase, such as P70 S6 kinase, more than inhibiting the activity of a second kinase, such as PI3K.

"Leukocytes" refers to cells in the blood, also termed "white cells," that are involved in defending the body against infective organisms and foreign substances. Leukocytes are produced in the bone marrow. There are five main types of leukocytes, subdivided into two main groups: polymorphonuclear leukocytes (neutrophils, eosinophils, basophils) and mononuclear leukocytes (monocytes and lymphocytes).

"Macrophages" refers to a population of ubiquitously distributed mononuclear phagocytes responsible for numerous homeostatic, immunological, and inflammatory processes. Their wide tissue distribution makes these cells well suited to provide an immediate defense against foreign elements prior to leukocyte immigration. Inflammatory macrophages are present in various exudates, and can be characterized by various specific markers, such peroxidase activity and cytokine expression, and are derived from monocytes they share similar properties. "Activated macrophages" refers to macrophages possessing specifically increased finctional activity. The process of differentiation is distinct from macrophage "activation," which is the process trough which differentiated macrophages acquire an increase ability to perform specific functions. Generally, unactivated macrophages are relatively quiescent immunologically, having low oxygen consumption, low levels of major histocompatibility complex (MHC) class II gene expression, and little or no cytokine secretion. Once activated, a macrophage has an inability to proliferate and has a high oxygen consumption. In addition, activated macrophages can be able to kill parasites and/or lyse tumor cells, and secretes cytokines such as TNF-α, IL-1 and IL-6.

"Mammalian Target of Rapamycin (mTOR)" refers to a polypeptide of approximately 289 kDa that shares approximately 45% identity with *S. cerevisae* Tor1 and Tor2 proteins. The human, rat, and mouse mTOR proteins share approximately 95% identity at the amino acid level. mTOR proteins are serine-threonine protein kinases (see Hunter et al., *Cell* 83:1-4, 1995; Hoekstra, *Curr. Opin. Genet. Dev.* 7:170-175, 1997). mTOR (see GenBank Accession No. L30475) phosphorylates P70 S6 kinase at theronine 389 and phosphorylates and activates the binding protein of eukaryotic translation initiation factor.

"Neoplasia" refers to the process of abnormal and uncontrolled growth of cells. The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant." Neoplasia is one example of a proliferative disorder.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilrns' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

"Parenteral" administration refers to administration outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intraarticularly, or subcutaneously, and various surface applications including intranasal, intradermal, and topical application, for instance.

"Phosphorylation" refers to the creation of a phosphate derivative of an organic molecule (such as a protein or a lipid). In a cell, this can be achieved by transferring a phosphate group from adenosine triphosphate (ATP).

A "proliferative disorder" is inclusive of neoplasms and restenosis.

"Restenosis" refers to the recurrence of narrowing after corrective surgery on the heart valve or the narrowing of a vascular structure (such as a coronary artery) following the removal or reduction of a previous narrowing. In several examples, restenosis occurs after the placement of a stent or following angioplasty.

"Sequence identity" refers to the similarity between amino acid sequences, and is expressed in terms of the similarity between the sequences, otherwise referred to as sequence identity. Sequence identity is frequently measured in terms of percentage identity (or similarity or homology); the higher the percentage, the more similar the two sequences are. Homologues or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.*, 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

"Homologues" and "variants" of a polypeptide refer to polypeptides characterized by possession of at least 75%, for example at least 80%, or at least 90% sequence identity counted over the full length alignment with the amino acid sequence of the polypeptide using the NCBI Blast 2.0, gapped blastp set to default parameters. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologues and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologues could be obtained that fall outside of the ranges provided.

"Transplantation" refers to the transfer of a tissue, cells, or an organ, or a portion thereof, from one subject to another subject, from one subject to another part of the same subject, or from one subject to the same part of the same subject. The donor and the recipient may or may not be of the same genotype. An "allogeneic transplant" or "heterologous transplant" refers to transplantation from one individual to another, wherein the individuals have genes at one or more loci that are not identical in sequence in the two individuals. An allogeneic transplant can occur between two individuals of the same species, who differ genetically, or between individuals of two different species. An "autologous transplant" refers to transplantation of a tissue, cells, or a portion thereof from one location to another in the same individual, or transplantation of a tissue or a portion thereof from one individual to another, wherein the two individuals are genetically identical.

The above term descriptions are provided solely to aid the reader, and should not be construed to have a scope less than that understood by a person of ordinary skill in the art or as limiting the scope of the appended claims.

The singular terms "a," "an," and "the" include plural referents unless context clearly indicates otherwise. Similarly, the word "or" is intended to include "and" unless the context clearly indicates otherwise. The word "comprises" indicates "includes." It is further to be understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting. All chemical compounds include both the (+) and (−) stereoisomers (as well as either the (+) or (−) stereoisomer), and any tautomers thereof. The abbreviation "mc" indicates "micro", thus "mcM" indicates micromolar and "mcL" indicates microliter."

Compounds of Use

One example of a class of 4H-1-benzopyran-4-one compounds useful in the methods and compositions disclosed herein are 2-(4-piperazinyl)-substituted 4H-1-benzopyran-4-one compounds that have a representative structure of:

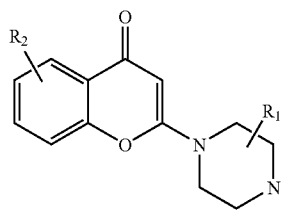

Formula A wherein the presence of each of $R_1$ and $R_2$ is optional and $R_1$ and $R_2$ are each independently selected from alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, halogen, hydroxy, amino, or thio. If $R_1$ and/or $R_2$ are present, there may be one or more $R_1$ and/or $R_2$ substituents on each respective ring structure.

An additional example of a class of 4H-1-benzopyran4-one compounds useful in the methods and compositions disclosed herein are 2-(4-piperazinyl)- 8-phenyl-4H-1-benzopyran-4-one compounds that have a representative structure of:

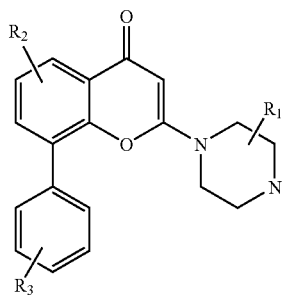

Formula B wherein the presence of each of $R_1$, $R_2$ and $R_3$ is optional and $R_1$ and $R_2$ are each independently selected from alkyl, aryl, alkoxy, halogen, hydroxy or amino. If $R_1$ and/or $R_2$ are present, there may be one or more $R_1$ and/or $R_2$ substituents on each respective ring structure.

An illustrative example of a specific 4H-1-benzopyran-4-one compound is 2-(4-piperazinyl)-8-phenyl4H-1-benzopyran4one that has a structure of:

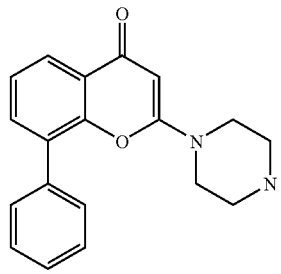

Formula C

The dihydrochloride salt of 2-(4-piperazinyl)-8-phenyl-4H-1-benzopyran4-one is commercially available from Sigma-Aldrich Corporation under the designation "LY 303511." The 2-(4-piperazinyl)-8-phenyl4H-1-benzopyran-4-one compounds described herein may be synthesized based on the procedures described in Vlahos et al., *J. Biol. Chem.* 269:5241-5248, 1994. Other salt forms of 2-(4-piperazinyl)-8-phenyl-4H-1-benzopyran-4one are readily synthesizable following known techniques such as those described in *Handbook of Pharmaceutical Salts, Properties, Selection and Use*, Wiley VCH (2002).

The presently disclosed methods include administering one or more of the presently described compounds, or a combination of one or more of the compounds and one or more other pharmaceutical agents, to the subject in a pharmaceutically compatible carrier. The administration is made in an amount effective to inhibit the development of proliferative disorders, such as neoplasms or restenosis, or to provide immunosuppression. Although the treatment can be used prophylactically in any patient in a demographic group at significant risk for such diseases, subjects can also be selected using more specific criteria, such as a definitive diagnosis of the condition.

The vehicle in which the drug is delivered can include pharmaceutically acceptable compositions of the drugs, using methods well known to those with skill in the art. Any of the common carriers, such as sterile saline or glucose solution, can be utilized with the drugs disclosed herein. Routes of administration include but are not limited to oral and parenteral routes, such as intravenous (iv), intraperitoneal (ip), rectal, topical, ophthalmic, nasal, and transdermal.

The drug may be administered in a suitable manner now known or later developed, e.g., orally or intravenously, in any conventional medium (see below). For example, intravenous injection may be by an aqueous saline medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives, surfactants, antioxidants (e.g., ascorbyl palmitate, butyl hydroxy anisole (BHA), butyl hydroxy toluene (BHT) and tocopherols), chelating agents, viscomodulators, tonicifiers, flavorants, colorants, odorants, and the like. A more complete explanation of parenteral pharmaceutical carriers can be found in *Remington: The Science and Practice of Pharmacy* (19*th* Edition, 1995) in chapter 95.

Examples of other pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions. Semi-solid formulations can be any semi-solid formulation including, for example, gels, pastes, creams and ointments. Liquid dosage forms may include solutions, suspensions, liposome formulations, or emulsions in organic or aqueous vehicles.

Methods of Suppressing an Immune Response or Treating a Proliferative Disorder

A method is provide herein for suppressing an immune response in a subject, comprising administering to the subject a therapeutically effective amount of a 2-(4-piperazinyl)-substituted 4H-1-benzopyran-4-one compound disclosed herein, or a pharmaceutically acceptable salt thereof. In one specific, non-lirniting example, the immune response can include the secretion of cytokines, such as, but not limited to, interleukin (IL)-12, tumor necrosis factor (TNF)-α, interferon (IFN)-γ, monocyte chemoattractant protein (MCP)-1, IL-10, IL-6. In another specific non-limiting example, the immune response includes macrophage activation.

The therapeutically effective amount of a 2-(4-piperazinyl)-substituted 4H-1-benzopyran4-one compound disclosed herein, or a pharmaceutically acceptable salt thereof, can be administered in conjunction with an additional immunosuppressive agent. This administration can be simultaneous or sequential, in any order. Immunosuppressive agents include, but are not limited to, Cyclosporine A, FK506, or analogs thereof, or antibodies such as a monoclonal antibody that specifically binds CD3 (such as OKT3), CD4, or CD8.

In one example, the 2-(4-piperazinyl)-substituted 4H-1-benzopyran-4-one compound and the immunosuppressive agent can be co-administered in solution, or in a delivery vehicle, such as a liposome, which would facilitate delivery and uptake of these agents.

In one embodiment, the methods disclosed herein can be used to treat transplant rejection. Transplantation involves the transfer of a tissue or an organ, or a portion thereof, from one body or part of the body to another body or part of the body. An "allogeneic transplantation" or a "heterologous transplantation" is transplantation from a donor to a recipient subject, wherein the donor and the recipient have genes at one or more loci that are not identical in sequence in the two individuals. The recipient can generate an immune response against donor antigens (including donor MHC); thus immunosuppressive therapy is often used to treat transplant recipients (such as heart, lung, or kidney transplant recipients). Disclosed herein is a novel method for treating transplant rejection that includes administering a therapeutically effective amount of a 2-(4-piperazinyl)-substituted 4H-1-benzopyran-4-one compound disclosed herein, or a pharmaceutically acceptable salt thereof. In one embodiment, treatment prolongs survival or improves function of the donor tissue. The methods disclosed herein can also be used to treat graft-versus-host disease.

A method is provided herein to treat a proliferative disorder, comprising administering to a subject a therapeutically effective amount of 2-(4-piperazinyl)-substituted 4H-1-benzopyran-4-one compound disclosed herein. It is demonstrated herein that 2-(4-piperazinyl)-substituted 4H-1-benzopyran-4-one compound can be used to inhibit proliferation of tumor cells. Thus, a therapeutically effective amount of the 2-(4-piperazinyl)-substituted 4H-1-benzopyran4-one compound can be administered to a subject to treat a tumor. Tumors include both benign and malignant tumors. Tumors further include hematological tumors and solid tumors. Exemplary tumors are tumors of the sldin, nervous system, lung, breast, reproductive organs, pancreas, lymphoid cells (including leukemias and lymphomas), blood or lymphatic vessels, and colon. Tumors include carcinomas, sarcomas, papillomas, adenomas, leukemias, lymphomas, melanomas, and adenocarcinomas, amongst others.

The therapeutically effective amount of a 2-(4-piperazinyl)-substituted 4H-1-benzopyran-4-one compound disclosed herein, or a pharmaceutically acceptable salt thereof, can be administered in conjunction with an additional chemotherapeutic agent. This administration can be simultaneous or sequential, in any order. Chemotherapeutic agents include, but are not limited to, chemical agents, anti-metabolites and antibodies. Exemplary chemotherapeutic agents are doxirubicin, paclitaxel, rapamycin, and methotrexate.

It is further demonstrated herein that 2-(4-piperazinyl)-substituted 4H-1 -benzopyran-4-one compound can be used to inhibit proliferation of smooth muscle cells. Thus, a therapeutically effective amount of the 2-(4-piperazinyl)-substituted 4H-1-benzopyran-4one compound can be administered to a subject to treat vascular restenosis.

The therapeutic compounds disclosed herein can be used to treat restenosis by administering the compound to the patient prior to, during and/or after coronary- or peripheral-artery angioplasty or atherectomy, coronary bypass graft or stent surgery, or peripheral vascular surgery (e.g., carotid or other peripheral vessel endarterectomy, vascular bypass, stent or prosthetic graft procedure). In addition to the administration techniques described elsewhere in this specification, the benzopyran-4-ones may be delivered via luminal devices such as vascular stents or grafts. For example, a stent or graft may be coated with or incorporate the benzopyran-4-one compound for controlled release of the benzopyran-4-one compound at the vascular site of interesl Such controlled release may include sustained compound delivery over a desired time period.

For use in any of the therapeutic methods disclosed herein, administration of the 2-(4-piperazinyl)-substituted 4H-1-benzopyran-4-one compound (and optionally additional agents) can be systemic or local. Local administration of the 2-(4-piperazinyl)-substituted 4H-1-benzopyran-4-one compound is performed by methods well known to those skilled in the art. By way of example, one method of administration to the knee, hip and/or shoulder of an individual, such as an individual with arthritis, is by intra-articular injection. For administration to the knee, for example, the joint to be injected is washed with a betadine solution or other antiseptic. A solution of about 1% lidocaine hydrochloride is injected into the skin and subcutaneous tissue. A 3-way stopcock/needle assembly is utilized to administer the compound via an 18-30 gauge needle. The 2-(4-piperazinyl)-substituted 4H-1-benzopyran4-one compound is injected into the joint space using a standard lateral approach well known to those skilled in the art. The needle and needle tract are cleansed by flushing with 1% lidocaine hydrochloride through the 3-way stopcock assembly as the needle is withdrawn. The knee is then moved through a flexion-extension arc and then immobilized in full extension. The patient is then confined to bed for approximately 24 hours to minimize movement and minimize leakage of the active agent from thejoint.

In other embodiments, the administration of the 2-(4-piperazinyl)-substituted 4H-1-benzopyran-4-one compound is systemic. Oral, intravenous, intra-arterial, subcutaneous, intra-peritoneal, intramuscular, and even rectal administration is contemplated.

Pharmacological compositions for use can be formulated in a conventional manner using one or more pharmacologically (e.g., physiologically or pharmaceutically) acceptable carriers comprising excipients, as well as optional auxiliaries that facilitate processing of the active compounds into preparations which can be used pharmaceutically. Proper formulation is dependent upon the route of administration chosen. In addition, one of skill in the art can readily select a suitable route of administration, including but not limited to intravenous, intramuscular, intraperitioneal, transmucosal, subcutaneous, transdermal, transnasal, inhalation, and oral administration.

Thus, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. A 2-(4-piperazinyl)-substituted 4H-1-benzopyran-4-one compound can also be formulated for use in inhalation therapy, such as for the treatment of subjects with inflammation of the lungs. For administration by inhalation, the active ingredient is conveniently delivered in the form of an aerosol spray presentation from pressurized packs or a nebuliser, with the use of a suitable propellant.

The 2-(4-piperazinyl)-substituted 4H-1-benzopyran-4-one compound can be formulated for parenteral administration by injection, e.g., by bolus injection or continuous infusion. Similarly, 2-(4-piperazinyl)-substituted 4H-1-benzopyran-4-one compounds can be formulated for intratracheal or for inhalation. Such compositions can take such forms as suspensions, solutions or emulsions in oily or aqueous vehicles, and can contain formulatory agents such as suspending, stabilizing and/or dispersing agents. Other pharmacological excipients are known in the art.

Therapeutically effective doses of the presently described compounds can be determined by one of skill in the art, with a goal of achieving a desired level of anti-restenosis, anti-atherosclerosis, anti-neoplasm or immunosuppression. The relative toxicities of the compounds make it possible to administer in various dosage ranges. In one example, the compound is administered orally in single or divided doses.

The specific dose level and frequency of dosage for any particular subject may be varied and will depend upon a variety of factors, including the activity of the specific compound, the extent of existing disease activity, the age, body weight, general health, sex, diet, mode and time of administration, rate of excretion, drug combination, and severity of the condition of the host undergoing therapy.

Screening

A method is provided herein for selecting an immunosuppressive agent or an anti-proliferative agent. The method includes selecting a test agent that preferentially inhibits mTOR-dependent phosphorylation of P70 S6 kinase as compared to phosphatidylinositol 3-kinase (PI3K) dependent phosphorylation of a substrate, thereby identifying a pharmaceutically useful immunosuppressive agent or anti-proliferative agent. In one embodiment, the agent also inhibits one or more additional kinases. For example, the agent can inhibit casein kinase 2, a regulator of cell proliferation. Thus, the method includes selecting a test agent that preferentially inhibits mTOR-dependent phosphorylation of P70 S6 kinase, casein kinase 2, or both, as compared to phosphatidylinositol 3-kinase (PI3K) dependent phosphorylation of a substrate, thereby identifying a pharmaceutically useful immunosuppressive agent or anti-proliferative agent. The assay can be performed in cells or cell extracts.

The test compound can be any compound of interest, including chemical compounds, small molecules, polypeptides or other biological agents (for example antibodies or cytokines). In several examples, a panel of potential chemotherapeutic agents, or a panel of potential immunosuppressive agents are screened. In other embodiments a panel of polypeptide variants is screened.

In assays that use cells, the cells are contacted with test compounds. In some embodiments, the cells are incubated with the test compound for an amount of time sufficient to affect phosphorylation of a substrate by PI3K and to inhibit phosphorylation of P70 S6 kinase in the cell. The cells are lysed and the amount of phosphorylated P70 S6 kinase and the amount of substrate phosphorylated by PI3K are measured. The amounts of phosphorylated P70 S6 kinase and the amount of phosphorylated substrate that is present in the cells is compared to identical cells that were not exposed to the test compound.

In some embodiments, Western blot technology is used with the cell proteins separated by electrophoresis and antibodies that bind to P70 S6 kinase, phosphorylated p70 S6 kinase, andlor antibodies that specifically bind the substrate (such as phosphorylated S6) are utilized. Alternatively, the cells may be incubated in the presence of orthophosphate containing a radiolabelled phosphorus, permitting the detection of phosphorylated or unphosphorylated substrate (such as P70 S6 kinase).

In some embodiments, cells are treated in vitro with test compounds at 37° C. in a 5% $CO_2$ humidified atmosphere. Following treatment with test compounds, cells are washed with $Ca^{2+}$ and $Mg^{2+}$ free PBS and total protein is extracted as described (Haldar et al., *Cell Death Diff.* 1:109-115, 1994; Haldar et al., *Nature* 342:195-198, 1989; Haldar et al., *Cancer Res.* 54:2095-2097, 1994). In additional embodiments, serial dilutions of test compound are used.

In some embodiments, phosphorylation is analyzed using Western blotting and immnunodetection which are performed using Amersham ECL an enhanced chemiluminescence detection system and well known methodology. In one example, phosphorylation of lymphoid cells can be carried out in phosphate free media (GIBCO) using 1 mCi/ml [$p^{32}$] orthophosphoric acid (NEN) for 6 hours in the presence of a test compound. Immunoprecipitation of $p^{32}$ labeled cellular extract can be performed, for example, as described in Haldar et al., *Nature* 342:195-198, 1998. This immunoprecipitation utilizes an antibody that binds a substrate of interest, such as P70 S6 kinase, a casein kinase 2 substrate (such as p53, Bid, DNA topoisomerase II), or a PI3K substrate (such as phosphatidylinositol, phosphatidylinositol 4-phosphate, phosphatidylinositol 4,5-phosphate). An immunocomplex is run on a 0.75 mm thick 10% SDS-PAGE. Subsequently, gels are dried and exposed for autoradiography.

Phospho-amino acid analysis can be performed as is known in the art. For example, the analysis can be performed essentially as described in the manual for the Hunter thin layer electrophoresis system, HTLE700, (CBS Scientific Company Inc., USA). Briefly, $P^{32}$ labeled immunoprecipitates are run on 10% SDS-PAGE gels. The immunoreactive bands of interest are cut out of the gel and eluted with 50 μM ammonium bicarbonate. After elution, the proteins are precipitated in the presence of 15%-20% TCA plus carrier protein, and washed with ethanol. Precipitated protein is then oxidized in performic acid and lyophilized. The dried pellet is resuspended in constant boiling HCI, heated at 110° C. and lyophilized. The residue is resuspended in pH 1.9 buffer (50 mcl formic acid, 156 mcl acetic acid, 1794 mcl $H_2O$) containing phospho-amino acid standards and spotted on a PEI cellulose plate. Two-dimensional thin layer chromatography is run using the pH 1.9 buffer for the first dimension and pH 3.5 buffer (100 ml acetic acid, 10 ml pyridine, 1890 ml $H_2O$) for the second. The plate is baked at 65° C. for 10 minutes, and the cold standards are visualized by spraying the plate with 0.25% ninhydrin and returning the plate to the 65° C. oven for 15 minutes. The plate is then exposed to film, such as to Kodak X-omat AR film, for two to four weeks.

In some embodiments, modulation of phosphorylation is analyzed using cell extract material as a starting material. Test compounds are combined with cell extract material and the effect of the compounds on phosphorylation of P70 S6 kinase and on phosphatidylinositol 3-kinase (PI3K)-dependent phosphorylation is examined. In one example, the cell extract material is contacted with test compounds to identify the effect the test compound has on phosphorylation of P70 S6 kinase in the presence of $^{32}$p-gamma -ATP, or to identify the effect the test compound has on phosphorylation of bcl-2.

In an exemplary protocol, cell extract is treated in vitro at 37° C. using 100 μg total cellular extract with a specified concentration of test compounds. For phosphatase reactions, 50 μl cell lysate is contacted with test compound and incubated with a reaction mixture for 30-60 minutes at 37° C.

For phosphorylation of cell extract material, 100 μg cellular extract is treated as described above except 40 μci [$^{32}$P]ATP (3000 Ci/mmol) are added to each reaction. Reactions are stopped by immersing the tubes in ice. The [$^{32}$P] ATP labeled reaction mixture is absorbed on immunoaffinity column made from the monoclonal antibody against P70 S6 kinase or a PI3K substrate by covalently binding purified antibodies to protein-A Sepharose using the crosslinker dimethylpimelimidate dihydrochloride (50 mM). Specifically bound [32 P]-labeled protein is eluted with 0.05 M diethylamine, pH 11.5 containing 0.5% Na-deoxycholate.

In exemplary methods, immunodetection by Western blotting is performed using Amersham ECL detection system and methodology known to one of skill in the art. Immunoprecipitation of $p^{32}$ labeled cellular extract can be performed, for example, as described in Haldar et al., Nature 342:195-198, 1989. The immunocomplex is run on a 0.75 mm thick 10% SDS-PAGE. Subsequently, gels are dried and exposed for autoradiography using film such as Kodak XAR film.

Phosphoaminoacid analysis can be performed essentially as described in the manual for the Hunter thin layer electrophoresis system, HTLE700, (CBS Scientific Company Inc., USA). In an exemplary method, $p^{32}$ labeled immunoprecipitates are run on 10% SDS-PAGE gels. The P70 S6 kinase immunoreactive bands are cut out of the gel and eluted with 50 μM ammonium bicarbonate. After elution the proteins are precipitated in the presence of 15%-20% TCA plus carrier protein, and washed with ethanol. Precipitated protein are then oxidized in performic acid and lyophilized. The dried pellet is resuspended in constant boiling HCl, heated at 110° C. and lyophilized. The residue is resuspended in pH 1.9 buffer (50 mcl formic acid, 156 mcl acetic acid, 1794 mcl $H_2O$) containing phospho-amino acid.standards and spotted on a PEI cellulose plate. Two dimensional thin layer chromatography is run using the pH 1.9 buffer for the first dimension and pH 3.5 buffer (100 ml acetic acid, 10 ml pyridine, 1890 ml $H_2O$) for the second. The plate is baked at 65° C. for 10 minutes, and the cold standards are visualized by spraying the plate with 0.25% ninhydrin and returning the plate to the 65° C. oven for 15 minutes. The plates are then exposed to film.

One specific assay for casein kinase 2 activity is available commercially as a kit from Upstate Biotechnology (New York). The assay is based on phosphorylation of a specific substrate (CK-2 substrate peptide) using the transfer of the gamma-phosphate of $^{32}$P-ATP by casein kinase 2 during a 10 minute incubation at 30° C. The phosphorylated substrate is then separated from the residual $^{32}$P-ATP using P81 phosphocellulose paper, and quantified by scintillation counting.

EXAMPLES

Rapamycin inhibits cancer and smooth muscle cell proliferation by blocking mTOR-dependent regulation of P70 S6 kinase. Rapamycin is approved by the FDA for the treatment of transplant rejection (imrnmunosuppressive action and anti-inflammatory), cancer, and vascular restenosis after coronary angioplasty. However, the use of rapamycin has several disadvantages and adverse effects, and it is desirable to identify other pharmacological inhibitors of mTOR-dependent signaling.

Like LY294002, LY303511 inhibits mTOR and casein kinase 2. Unlike LY294002, LY303511 fails to significantly inhibit PI3K, an important signaling enzyme in the control of cell death, cytokinesis, and glucose/lipid metabolism. Wortmannin is selective for PI3K The examples disclosed herein use LY303511 as an exemplary 4H-1-benzopyran-4-one compound. The results demonstrate that LY303511 can be used to suppress an immune response and to inhibit proliferation of cells, including smooth muscle cells and tumor cells. It is likely that LY303511 selectively inhibits mTOR at a site different from that involved in rapamycin binding, with fewer effects on PI3K. LY303511 can be used alone, or in combination with rapamycin or other agents to control cell proliferation and the immune response.

Example 1

LY303511 Inhibits Cell Proliferation

Figure 1:
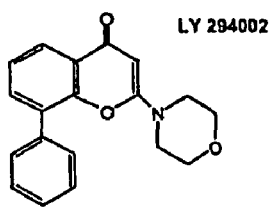
FIG. 1A is the chemical Structures of LY294002 and LY303511. The morpholino oxygen in LY294002 is replaced by an amine in LY303511.
FIG. 1B is a digital image showing results wherein A549 cells were incubated without or with 100 µM LY303511, rapamycin, 200 ng/ml, or 200 nM wortmannin, (or in the digital image shown in FIG. 1C and the bar graph and digital image shown in FIG. 1D.
Figure 1:
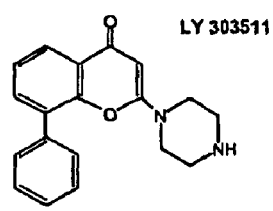
Figure 1:
Figure 1:
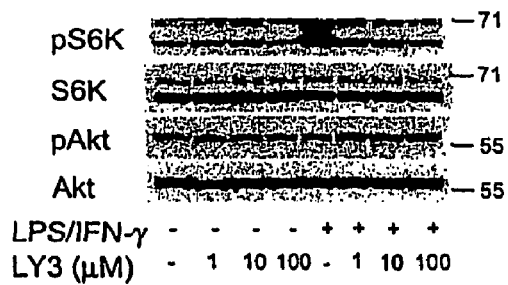
Figure 1:
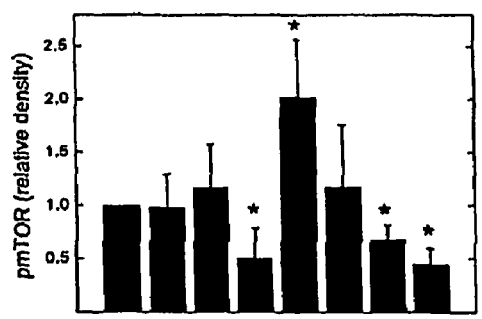
Figure 1:
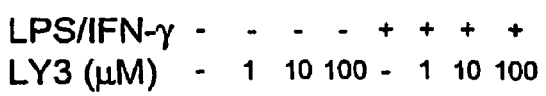

This example demonstrates that LY303511 blocks phosphorylation of P70 S6 kinase and cell proliferation in human lung epithelial adenocarcinoma (A549) cells. LY303511 differs from LY294002 by an oxygen substitution that replaces the morpholino oxygen with an amine (FIG. 1A).

A549 cells were treated without or with 100 mcM LY303511, 200 ng/ml rapamycin, or 50 nM wortmannin in serum free media for 1 hour before addition of E. coli lipopolysaccharide (LPS), 1000 mcglml and interferon (IFN)-γ, 100 U/ml (LPS/IFN-γ or "L/I"). Cells were homogenized and the indicated proteins (see Table 1) were detected by Western blot. Western blots are from the same experiment, and representative of three experiments.

TABLE 1

| Description of antibodies | | |
|---|---|---|
| | Epitope | Significance |
| pS6K | Phospho threonine residue at T389 in P70 S6 kinase. | Regulated by mTOR |
| pAKT | Phospho serine residue at S473 in AKT. | Regulated by PI3K |

TABLE 1-continued

Description of antibodies

| | Epitope | Significance |
|---|---|---|
| pmTOR | Phospho serine residue at S2481 in mTOR. | Autophosphorylation site regulated by mTOR kinase activity |
| mTOR | Total mTOR | N/A |
| pRb | Phospho-serine residues at S807 and S811 in Rb | Cell cycle-dependent phosphorylation |

The results demonstrated that LY303511 blocks phosphorylation of P70 S6 kinase (FIG. 1B). Wortmannin and rapaycin also blocked phosphorylation. The results demonstrated that LY303511 and rapamycin increase phosphorylation of AKT (FIG. 1B). Wortmannin blocks PI3K and inhibits the phosphorylation of pAKT. Thus, LY303511 inhibits mTOR-sensitive phosphorylation of S6 but not AKT (FIG. 1C). These results indicate that LY303511 is a mTOR inhibitor. The results also demonstrated that LY303511 inhibits autophosphorylation of mTOR in a concentration-dependent fashion (FIG. 1D). Unlike rapamycin, LY303511 had minimal effects on basal phosphorylation of S6K or mTOR (FIG. 1B, 1D). Thus, LY303511 inhibited LPS/IFNγ-stimulated mTOR activity and mTOR-dependent phosphorylation of S6K in PI3K-independent fashion, and at concentrations as low as 1 μM.

In a further experiment, A549 cells were plated at 4,000 cells per well in a 96-well place and treated with bromodeoxyuridine for 24 hours without or with pharmacological inhibitors as indicated. Bromodeoxyuridine (BrdU) uptake, an indicator of DNA synthesis and cell proliferation, was measured by in situ ELISA (BrdU detection kit, Roche).

Additionally, A549 cells (80,000 cells per well), were grown for 24 hours before addition of inhibitors (FIG. 2A). After 24 hours, trypan blue-stained cells were counted using a hemocytometer. Cell viability was >99% under all conditions (data not shown). In cells exposed to vehicle alone, cell number increased by ~50% over 24 hours. Rapamycin slightly attenuated cell proliferation, whereas LY303511 had a significant inhibitory effect, almost equal to that of LY294002. Consistent with PI3K-independent effects of LY303511 and LY294002, wortmannin did not significantly reduce A549 cell proliferation. LY303511 did not induce apoptosis or necrosis as determined by flow cytometric analysis of propidium iodide-stained cells As determined by bromodeoxyuridine (BrDu) uptake, LY303511 as well as a combination of LY303511 and rapamycin inhibited proliferation of A549 cells (FIG. 2B). Whereas rapamycin had a weak but statistically significant effect on DNA synthesis, administration of LY303511 led to a concentration-dependent reduction (FIG. 2B). There was no additional effect when LY303511 was combined with rapamycin. DMSO alone had no effect on A549 cell proliferation.

In another experiment, A549 cells were grown to subconfluence in serum-containing media, and incubated with a vehicle, 100 mcM LY303511, or rapamycin, 200 ng/ml for 0, 12, or 24 hours. Cells were lysed, and proteins separated by SDS-PAGE before transfer to nitrocellulose membranes. Membranes were incubated with antibodies against p27Kip1, p21 Cip1 orphospho-P70 S6 kinase T389.

At 12 and 24 hours after treatment, LY303511 and rapamycin blocked phosphorylation of P70 S6 kinase at T389, consistent with inhibition of mTOR kinase activity (FIG. 3A); LY303511, but not rapamycin, led to the accumulation of p27Kip1, and p21 Cip1, markers of cell cycle arrest. The LY303511-dependent in increase in p27 Kip1 (p27) levels indicates an effect on inhibitors of G1/S transition similar to that of rapamycin (FIG. 3A). In contrast to rapamycin, however, LY303511 caused a significant increase in p21 Cip1 (p21), an inhibitor of late S phase progression (FIG. 3A). LY303511, but not rapamycin, decreased levels of cyclin A and B, which are also regulators of S and G2/M phase progression (FIG. 3B). LY303511 also reduced the phosphorylation of Rb, which suggests that the mechanism of cell cycle inhibition was, in part, due to inhibition of E2F-dependent genes. These results support a role for LY303511-sensitive kinase(s) in late S and G2/M progression, in addition to G1/S transition.

To confirm that LY303511 led to G1 arrest, A549 cells were treated with 0, 10, or 100 mcM LY303511 for 24 hours, fixed, and incubated with antibodies against KI-67. Slides were mounted in solution containing DAPI to stain nuclei. Photos were captured using equal laser intensity and gain. Treatment with LY303511, but not rapamycin, led to a significant decrease in whole cell KI-67 levels, which is also consistent with a block in cell proliferation.

The results demonstrated that LY303511 inhibited basal and stimulated phosphorylation of P70 S6 kinase at threonine (T) 389 (T389), a marker of mTOR-dependent P70 S6 kinase activation. In addition, LY303511 did not inhibit PI3K-dependent phosphorylation of AKT at serine (S) 473 (S473). Similar to rapamycin, LY303511 increased AKT phosphorylation. In addition, LY303511 inhibited basal and stimulated phosphorylation of mTOR at serine 2481 (S2481), a marker of mTOR kinase activity. LY303511 also inhibited proliferation in A549 cells. The effect was additive with rapamycin at doses of LY303511 between 10 and 100 mcM. Thus, LY303511, or combinations of LY303511 and rapamycin, can be used to inhibit the growth of adenocarcinoma cells. The results further demonstrate that cell cycle arrest was induced.

Example 2

LY303511 Inhibits the Activation of an Inflammatory Process

This example demonstrates that LY303511 inhibits phosphorylation of P70 S6 kinase and activation of STAT1 in response to LPS and IFN-γ in A549 cells.

Figure 8:
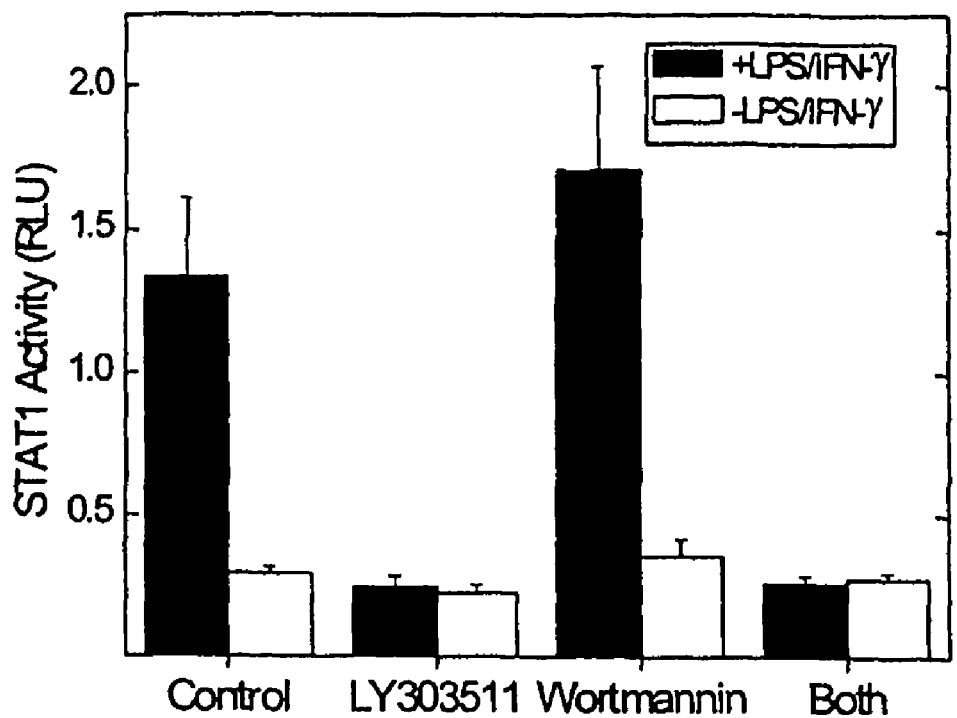
Figure 8:
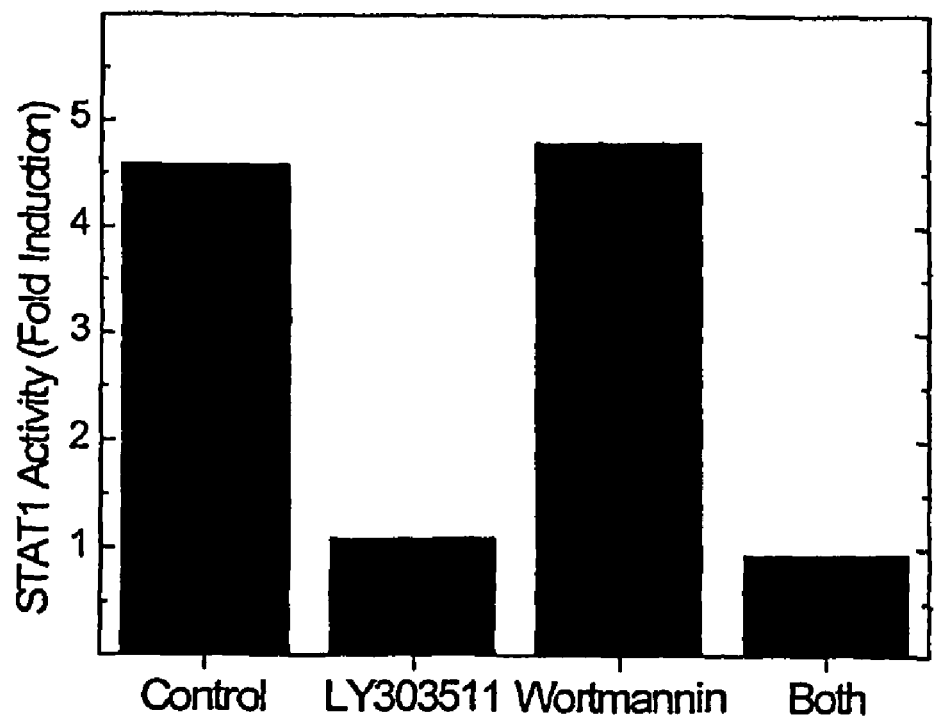

A549 cells were transiently transfected with a reporter vector expressing firefly luciferase driven by STAT1 (GAS-luc, Clontech), and incubated without or with 100 mcM LY303511, rapamycin, 200 ng/ml, or both, for 1 hour before addition of LPS/IFN-γ for 6 hours. STAT1 activity (luciferase activity) was measured in cell lysates (RLU). The data presented in FIG. 8 are triplicate samples±SEM, and are representative of two independent experiments. LY303511 inhibited STAT1 activation by two inflammatory mediators, LPS/IFN-γ.

Consistent with inhibition of transcription factor STAT1, LY303511 decreased LPS-induced cytokine production by macrophages stimulated with LPS (see Example 8).

Example 3

LY303511 Inhibits Phosphorylation of P70 S6 Kinase in Smooth Muscle Cells

This example demonstrates that LY303511 inhibits phosphorylation of P70 S6 kinase in primary human pulmonary artery smooth muscle (HPASM) cells.

HPASM cells were purchased from Clonetics and passaged according to the manufacturer's instructions. Cells were plated in 100 mm dishes, and allowed to grow to near confluence before serum starvation for 24 hours. Inhibitors were added to the media 1 hour before the addition of 10% FBS for 30 minutes. Cells were homogenized and the indicated proteins were detected by Western blot.

LY303511 inhibited basal and serum-stimulate phosphorylation of P70 S6 kinase in human pulmonary artery smooth muscle (PASM) cells (FIGS. 4A and 4B). LY303511 also inhibits phosphorylation of AKT, albeit to a lesser extent than phosphorylation of p70 S6 kinase (FIG. 4B). LY303511 also inhibited serum-stimulated phosphorylation of mTOR at S2481, a marker of mTOR kinase activity.

In PASM cells incubated with serum before addition of inhibitors, rapamycin had little effect on proliferation, whereas LY303511 inhibited in concentration-dependent fashion (FIG. 4C). The effect of rapamycin on proliferation (BrDu incorporation), without or with LY303511, was enhanced when PASM cells were incubated in serum-free medium for 24 h before addition of FBS (FIG. 4D). The effect of LY303511 on PASM cell proliferation, like that of rapamycin, was enhanced in the absence of serum. The effect on proliferation of 10 μM LY303511 and rapamycin, 200 ng/ml, were additive to that of 10 μM LY303511 alone (p<0.05, FIG. 4C, D). Although Akt phosphorylation was inhibited by LY303511 (FIG. 4B), wortmannin did not inhibit cell proliferation, indicating that this effect of LY303511 was independent of PI3K.

The effects of rapamycin and LY303511 on cell cycle were less pronounced in PASM than in A549 cells (FIG. 5A). Incubation with rapamycin or serum free-medium led to G1 arrest. In contrast, LY303511 reduced the proportion of cells in S phase by increasing the fraction in G1 and G2/M phase. The effects of rapamycin plus LY303511 on the reduction of S phase cells were additive. However, the increase in G1 smooth muscle cells in response to LY303511 was negligible, indicating a greater effect of LY303511 in cancer cells than in primary cells.

Thus, LY303511, or combinations of LY303511 and rapamycin, can be used to inhibit the growth of primary smooth muscle cells. The results further indicate LY303511 can be used to induce cell cycle arrest of these cells.

Example 4

LY303511 Inhibits the Cell Cycle by Causing Combined G1 and G2 Arrest

In order to investigate the effect of LY303511 on the cell cycle, A549 cells or pulmonary artery smooth muscle cells were grown to sub-confluence in serum-containing media, and incubated with vehicle, 10, or 100 mcM LY303511, without or with Rapamycin (200 ng/ml), for 24 hours. The cells were then harvested and stained with propidium iodide before cell cycle analysis by flow cytometry. The proportion of cells in G1, S, or G2/M phase of the cell cycle for each experimental condition was determined. Cells were gated by intensity of propidium iodide staining to determiine the proportions of cells in G1, S, or G2/M phase of the cell cycle. Consistent with an effect on DNA synthesis, 100 μM LY303511 significantly reduced the fraction of cells in S phase (FIG. 2C). The proportion of cells in G2/M remained unchanged, indicating that cells were arrested in both G1 and G2/M. In contrast, rapamycin increased the G1 population by reducing the proportion of cells in both S and G2/M. The effects of 10 μM LY303511 and rap amycin on the reduction in S phase cells were additive to that of 10 μM LY303511 alone (P=0.056, FIG. 2C). The greater reduction in S phase cells produced by adding LY303511 to rapamycin occurred without a further decrease in G2/M, indicating that LY303511 blocks the cell cycle by an additional mechanism that differs from that used by rapamycin.

The results demonstrate that LY303511 causes cell cycle arrest in both transformed cells and pulmonary artery smooth muscle cells. Since, unlike rapamycin, LY303511 leads to an increase in cells in G2/M phase, the results also suggest that there could be additional mTOR-independent cellular targets for LY303511 (e.g., casein kinase 2).

Example 5

LY303511 Inhibits Casein Kinase 2 (CK2) Activity

Microarray gene expression analyses have been performed in which A549 cells were incubated without or with LY294002 or wortmannin for 1 hour before the addition of L/I for 6 hours. By cellular feedback mechanisms, the levels of mRNA encoding proteins that are directly inhibited by a pharmacological agent might be increased in the presence of that agent. To identify additional kinase targets for LY294002 that are PI3K-independent, mRNAs that were increased by LY294002, and not by wortmannin, were identified from the dataset by filtering and statistical analysis. As expected, the levels of mTOR mRNA were increased in the presence of LY294002 (1.7-fold), and not by wortmannin. The mRNAs of other kinases that were increased by LY294002 included that encoding CK2α' (1.8-fold; GenBank accession #M55268). Since CK2 can regulate both G1 and G2/M cell cycle transitions, the effects of LY294002 and LY303511 on CK2 activity were assessed.

Casein kinase 2 (CK2) activity (counts per minute) was measured using a casein kinase 2 activity kit (Upstate Biotechnology catalogue number 17-132) by incubating recombinant 100 ng CK2, magnesium/ATP cocktail (10 mcCi $^{32}$P-garnma-ATP, 0.675 micromoles $MgCl_2$, 4.5 nmoles ATP), and 10 micromoles peptide substrate (arnino acid sequence RRRDDDSDDD (SEQ ID NO: 1) in 50 mcl assay buffer without or with the indicated concentrations of DMSO (1%), LY294002, LY303511, or rapamycin for 10 minutes at 30° C. Assays were stopped with 20 mcl of 40% trichloroacetic acid, and 25 mcl were spotted on P81 phosphocellulose paper squares before washing 3 times with 0.75% phosphoric acid, and once with acetone. 32P incorporation on the substrate peptide was detected by counting the phosphocellulose squares in 5 ml scintillation fluid using a Packard 100 Tri-Carb liquid scintillation counter.

Incubation of recombinant CK2 with LY303511 or LY294002 led to a concentration-dependent inhibition of CK2 activity (FIG. 5B). The approximate $IC_{50}$ for LY294002 (10 μM) was one tenth that for LY303511. Neither wortmannin nor rapamycin affected CK2 activity. Since CK2 is known to regulate G1 and G2 progression in intact cells, CK2 represents an additional kinase target for LY303511. Thus, LY303511 inhibits casein kinase 2 with $IC_{50}$ between 10 and 100 mcM. LY303511 preferentially inhibits P70 S6 kinase and casein kinase 2 as compared to PI3K.

The ability of LY303511 and LY294002 to inhibit CK2 in vitro suggests a second mTOR- and PI3K- independent mechanism by which these inhibitors might block cell proliferation. These results establish a novel family of compounds that might be useful for the treatment of neoplastic disorders.

The finding that LY303511 and LY294002 block CK2 activity suggests a new alternative target for this class of drugs, and is consistent with an mTOR-independent mechanism for the inhibition of cell proliferation and cell cycle regulation. CK2 is a ubiquitous and highly conserved serine/threonine kinase that is required for cell survival. In general, tumor cells exhibit high levels of CK2 activity, and CK2 overproduction is capable of inducing tumorigenesis in p53- deficient mice. CK2 protects cells from apoptosis by directly phosphorylating proteins such as p53, BH3-only proapoptosis protein (BID), β-catenin, or Fas-associated factor (FAF1). In addition, CK2 regulates progression through the G0/G1, G1/S, and G2/M checkpoints. LY303511-induced reduction in cyclin A and B levels, as well as the increase in p21 and p27 levels (FIG. 3), is consistent with CK2-dependent blockade of the cell cycle. The additive effect of LY303511 on proliferation and cell cycle indicates that, in addition to inhibiting mTOR phosphorylation of S6K, LY303511 can overcome resistance to rapamycin by inhibiting a pathway other than S6K, such as CK2.

mTOR and PI3K fall within the phosphatidylinositol 3- and 4-kinase family of proteins (interpro family PI3_PI4_kinase, number IPR000403, see the InterPro database, available on the internet). This family includes 247 proteins with specific signature sequences for the PI3K domain. LY294002 inhibits PI3K and mTOR, while other analogues (such as LY303511) could preferentially inhibit a subset of kinases in the family. Given the structural homology between the PI3K-catalytic domains in mTOR and PI3K, LY303511 could also inhibit other kinases with PI3K-like domains; these include the following:

| Kinase | GenBank Accession Number |
| --- | --- |
| phosphatidylinositol 3-kinase-related protein kinase | BAB70696 |
| PI-3-kinase-related kinase SMG-1 isoform 1 | NP_055907 |
| PI-3-kinase ATX | AAM73708 |
| KIAA0421 | BAA24851 |
| LIP isoform of BLIP | AAK58892 |
| ataxia telangiectasia and Rad3 related protein | NP_001175 |
| ataxia telangiectasia mutated protein isoform 1 | NP_000042 |
| ATM | AAB65827 |
| DNA-dependent protein kinase | AAK40350 |
| transformation/transcription domain-associated protein | NP_003487 |
| Phosphatidylinositol 4-kinase beta | Q9UBF8 |

Example 6

Determination of the IC50 for Inhibition of Phosphorylation

In A549 cells, the $IC_{50}$ for LY303511-mediated inhibition of S6K phosphorylation in stimulated cells is approximately 10 mcM by densitometric analysis of pS6K phosphoblots. LY303511 does not inhibit phosphorylation of Akt when A549 cells are contacted with the drug, even at 100 mcM. In pulmonary artery smooth muscle cells, the $IC_{50}$ for LY303511-mediated inhibition of S6K phosphorylation is approximately 1 mcM by densitometry. The $IC_{50}$ for LY303511-mediated inhibition of Akt phosphorylation is between 10 and 100 mcM by densitometry (see FIGS. 8A-D).

Example 7

Effect of LY303511 Alone or in Combination with Doxorubicin on Prostate Cancer

In Vivo Model System

Male adult nude mice are fed a standard diet and housed in common cages. Five mice are included per treatment group for a total of 100 mice. Each mouse is inoculated subcutaneously with $1 \times 10^6$ cells PC-3 (prostate cancer) cells in PBS containing 20% matrigel. After the tumor reaches ~200 mm³ in size, a vehicle (0.2% DMSO or saline) or drug is administered once per day for 5 days, and tumor volume is measured every 2 days for 33 days prior to death or euthanasia by carbon dioxide inhalation.

Five mice are assigned to each treatment group as follows:

|   | Rapamycin (mg/kg) | LY303511 (mg/kg) | LY303511 Rapamycin (3 mg/kg) | Rapamycin (mg/kg) + Doxorubicin (10 mg/kg) | LY303511 (mg/kg) + Doxorubicin (10 mg/kg) | LY3 + Rapamycin (3 mg/kg) + Doxyrubicin (10 mg/kg) |
| --- | --- | --- | --- | --- | --- | --- |
| N = 20 | 0 | 0 | — | 0 | 0 | — |
| N = 30 | 1.5 | 1 | 1 | 1.5 | 1 | 1 |
| N = 30 | 3.0 | 10 | 10 | 3.0 | 10 | 10 |
| N = 20 |  | 100 | 100 |  | 100 | 100 |

Doxorubicin or a vehicle is administered on day 1 only. Rapamycin or LY303511 is administered daily and intraperitoneally from days 1-5 as previously described (see Grunwald et al., Cancer Res 62:6141, 2002). The protocol ends 33 days after the beginning of drug treatment. After euthanasia or death, tumors are excised for histological analysis, immunohistochemistry, and Western blotting.

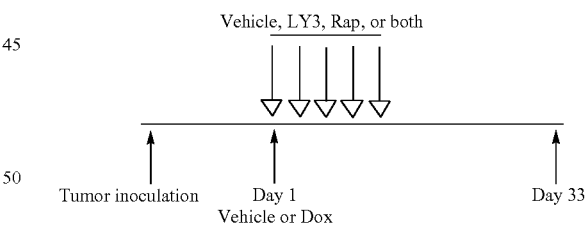

The effect of LY303511 on tumor growth was assessed in vivo. Human prostate adenocarcinoma cells (PC-3 cells, ATCC No. CTL-1435) were culture in vitro 5 before harvesting and implantation. For each mouse, $1 \times 10^6$ cells in 20% Matrigel™ (matrix) were implanted by subcutaneous injection into the flank. Mice were subdivided into six groups of ten mice each. Treatment protocols were begun (Day 1) when tumors reached approximately 150 mm³, and tumor volumes (=Caliper length×width²/2) were measured for thirty days at the indicated time points. Data were expressed as the average tumor volume +/− SEM for each treatment group and time point. The data is shown both in FIG. 6A and 6B. (*p<0.05 by one way ANOVA for inter-group comparisons at each time point. FIG. 6C is a Kaplan-meier analysis, representing the probability that tumor volumes are less than 300 mm³ at any given time point (p<0.001 by log-rank test for inter-group comparison).

The following treatments were assigned to each group:

| Group | LY303511 (10 mg/kg) | Doxorubicin (10 mg/kg) |
|---|---|---|
| 1 | None | None |
| 2 | Daily for 5 days | None |
| 3 | Daily for 10 days | None |
| 4 | Daily for 20 days | None |
| 5 | None | Once on Day 1 |
| 6 | Daily for 10 days | Once on Day 1 |

LY303511 inhibited the growth of prostate adenocarcinoma cells (PC-3) cells in nude mice. LY303511, 10 mg/kg was administered intraperitoneally to attenuate PC-3 tumor growth in nude mice. The degree of growth inhibition was direct proportional to the duration of treatment. A 20 day course of LY303511 (LY3) was as effective at inhibiting tumor growth as a ten day course (see FIG. 6C). After 21 days, greater than 15% of the mice required euthanasia because of excessive tumor growth, and the average tumor volume measurements became too variable.

The results demonstrate that LY303511, or a combination of LY303511 and Doxorubicin, decrease tumor burden (FIGS. 6A and 6B). Thus, LY303511, and/or LY303511 combined with an additional chemotherapeutic, can be used to treat a proliferative disorder, such as cancer. LY303511 can also be combined with rapamycin for tumor treatment.

Example 8

Use of LY303511 to Suppress an Immune Response

The pathogenesis of a variety of human diseases including multiple sclerosis (MS), rheumatoid arthritis, diabetes, autoimmune uveitis, transplant rejection, chronic beryllium disease and graft-versus-host disease appear to a T cell-mediated immune response. The compounds disclosed herein can be of use to treat these disorders.

TABLE 2

Examples of Human Autoimmune Disorders

| Human Disease | Animal Model |
|---|---|
| Multiple Sclerosis | experimental autoimmune encephalitis (EAE) mouse model and Lewis rat |
| Diabetes | NOD mice |
| Arthritis and related MCTD (mixed connective tissue disease) | Chicken, Mice and Rats |
| Hashimoto's Thyroiditis, Grave's Disease | Mice, Lewis Rats, and OS chickens |
| Uveitis | Mice |
| Inflammatory Bowel Disease | MDrla Knockout Mice |
| Polyarteritis | Mice |
| Myasthenia Gravis | Mice |
| Transplantation rejection | Mice |
| | Islet cell transplantation |

There are several animal based autoimmune models that can be used to test the use of the compounds disclosed herein for the treatment of an autoimmune disorder. Table 2 lists several exemplary immune-mediated disorders that can be treated using a peptide/MHC complex. For example, the non-obese diabetic (NOD) mouse model is an animal model system wherein animals develop diabetes with increasing age. To test the efficacy of a particular compound, groups of animals at the prediabetic stage (4 weeks or younger) are treated with, for example, LY303511, or LY303511 in combination with an additional immunosuppressive agent. The number of animals developing diabetes, and the rate that the anirnals develop diabetes, is then analyzed. Similarly, in the Hashimoto's mouse model system, to test the efficacy of a vaccine, groups of animals prior to the development of symptoms are treated with a treated with, for example, LY303511, or LY303511 in combination with an additional immunosuppressive agent. The number of animals developing the disease, and the rate that the animals develop the disease, are then analyzed.

In the NOD model or in the Hashimoto's model, or any other model system, LY303511, or LY303511 in combination with an additional immunosuppressive agent, delays the progression of the disease, or provides protection from developing the disease, when compared to untreated animals.

In order to demonstrate the effect of LY303511 on an immune response, wild type mice from Jackson (Jac) and Taconic (Tac) were used. Peritoneal macrophages were harvested three days after thioglycolate injection. Cells were incubated for three days in 2% FCS RPM. The supernatant was collected after stimulation with LPS 1 μg/ml with or without LY 303511 (1~100 μM) or DMSO for 24 hours. Cytokines (interleukin (IL)-12p70, tumor necrosis factor (TNF)-α, interferon (IFN)-γ, monocyte chemoattractant protein (MCP)-1, IL-10, IL-6) were measured in cell supernatants. The results demonstrated that LY303511 caused a dose-dependent reduction of all six cytokines (see FIG. 7A-F). Addition of 100 μM LY303511 resulted in cytokine secretion similar to background levels. Thus, LY303511 clearly can reduce cytokine expression, and has an anti-inflammatory effect.

Example 9

Materials and Methods

The following provides a summary of materials and methods were used in the above Examples; this section provided to consolidate this information in a single section.

Cell Culture: A549 cells (CCL 185, American Type Culture Collection (ATCC); Manassas, Va.), a human alveolar type II epithelial cell-like lung adenocarcinoma cell line, were grown at 37° C. with 5% $CO_2$ in Ham's F-12 K medium supplemented with 10% fetal bovine serum (FBS), 2 mM glutamine, penicillin (100 units/ml), and streptomycin (100 μg/ml), all from Biofluids (Rockville, Md.). Human pulmonary artery smooth muscle (PASM) cells (Cambrex; Rockland, Me.) were grown at 37° C. with 5% $CO_2$ in SMG2 medium supplemented with 5% FBS, insulin, fibroblast growth factor, epidermal growth factor, and gentamycinl/amphotericin as per the manufacturer's instructions.

Pharmacological inhibitors and antibodies: LY303511, rapamycin, LY294002, and wortrnannin were purchased from Biomol (Plymouth, Pa.) or Calbiochem (San Diego, Calif.), and dissolved in DMSO. Antibodies against phospho-S6K T389, phospho-Akt S473, phospho-mTOR S2481, phospho-Rb S807/S811, S6K, and Akt were purchased from Cell Signaling Technologies (Beverly, Mass.). Monoclonal antibodies against mTOR (RAFT1), cyclin A, cyclin B, Cyclin D, Cyclin E, p27 Kip1, and p21 Cip1 were purchased from BD Transduction Laboratories (San Diego, Calif.).

Measurement of protein phosphorylation: A549 cells were incubated in serum-free medium without or with inhibitors for 1 hour, as indicated, before incubation for 30 minutes with a mixture of LPS, 100 µg/ml (Sigma; St. Louis, Mo.) and IFN-γ, 100 U/ml (Roche; Nutley, N.J.). PASM cells were incubated in serum-free medium without or with inhibitors for 24 h as indicated, before incubation for 30 min with 10% FBS. A549 or PASM cells were washed once with cold PBS and incubated for 15 minutes on ice ih lysis buffer (20 mM Tris pH 8.0, 1% Nonidet P-40, 1 mM EDTA, 5 mM benzamidine, aprotinin, 10 µg/ml, leupeptin, 10 µg/ml, trypsin soybean inhibitor, 1 mM PMSF, 50 mM sodium fluoride, 100 µM sodium orthovanadate, and 1:100 Sigma phosphatase inhibitor set I containing cantharidin, microcystin LR and bromotetramizole). After freezing and thawing, lysates were centrifuged for 30 min at 16,000×g before protein measurement and storage at −80° C. Equal amounts of total protein were separated by SDS-PAGE, and transferred to a nitrocellulose membrane, before immunoblotting with primary antibodies as indicated. Membranes were treated with anti-rabbit IgG or anti-mouse IgG antibodies (Promega; Madison, Wis.) linked to horseradish peroxidase, developed using an enhanced chemiluminescence detection kit (SuperSignal West Pico, Pierce; Rockford, Ill.), and exposed to X-ray film, which was scanned using an Epson Expression 636 scanner. Integrated band densities were quantified using Scion Image beta 3b software.

Measurement of cell proliferation:. Cell proliferation, or DNA synthesis, was estimated using an in situ 5-bromo-2-deoxy-uridine (BrDU) detection kit as per the manufacturer's instructions (Roche Diagnostics; Nutley, N.J.). Briefly, A549 or PASM cells (4,000/well) were seeded in 96-well plates, and grown for 24 hours in the presence of serum. 10 mM BrDU was added for 24 hours without or with inhibitors as indicated. In some experiments, PASM cells were incubated in serum-free medium for an additional 24 h before addition of BrDU and inhibitors. Cells were fixed, and BrDU was detected using a peroxidase-conjugated anti-BrDU antibody. The measured absorbance data in cells treated with inhibitors were normalized to those treated with DMSO control (% control).

Measurement of cell cycle: A549 or PASM cells were grown to 80% confluence before addition of inhibitors as indicated for 24 hours. Cells were harvested by gentle trypsinization, and washed three times with PBS before addition of 0.5 ml Vindalov's propidium iodide (10 mM Trizma base, 10 mM NaCl, 0.05 mg/ml propidium iodide, 0.7 U/ml RNAse, 0.1% Nonidet P40) for at least 2 hours. Cell cycle analysis was performed on a FACSCalibur flow cytometer (BD Biosciences; San Diego, Calif.). The 488-nm line from an argon laser was used for excitation of the propidium iodide, and the emitted fluorescence was collected using a 585-nm band pass filter (FL2). Listmode data were collected on a linear scale using Cell Quest Software. Propidium iodide-stained cells were counted by flow cytometry, and the percentage of cells in G1, S, or G2/M phase was determined.

Measurement of casein kinase 2 (CK2) activity: CK2 activity (counts per minute) was measured using a CK2 activity kit (Upstate, Charlottesville, Va.) by incubating 100 ng of recombinant CK2, rnagnesium/ATP cocktail (10 µCi $^{32}$P-gamma-ATP, 0.675 µmol MgCl$_2$, 4.5 nmol ATP), and 10 µmol peptide substrate (amino acid sequence RRRDDDSDDD) in 50 µl assay buffer (20 mM MOPS, pH 7.2, 5 mM EGTA, 25 mM β-glycerol phosphate, 1 mM sodium orthovanadate, 1 mM dithiothreitol) without or with the indicated concentrations of LY294002, LY303511, wortmannin or rapamycin in 1% DMSO for 10 min at 30° C. Assays were stopped with 20 µl of 40% trichloroacetic acid, and samples (25 µl) of supernatant were applied to P81 phosphocellulose paper squares, which were then washed three times with 0.75% phosphoric acid, and once with acetone. $^{32}$P in the substrate peptide was quantified using a Packard 100 Tri-Carb liquid scintillation counter on phosphocellulose squares in 5 ml of scintillation fluid. Activity is expressed as pmol phosphate incorporated per 10 minutes. CK2 activity measured in the presence of inhibitors was divided by that measured for the DMSO control (=100% control).

Having illustrated and described the principles of the disclosed compositions and methods, it will be apparent that these compositions and methods may be modified in arrangement and detail without departing from such principles.

What is claimed is:

1. A method of inhibiting proliferation of a cell, comprising contacting the cell with an effective amount of a 2-(4-piperazinyl)-substituted 4H-1-benzopyran-4-one compound, or a pharmaceutically acceptable salt thereof, having the structure of

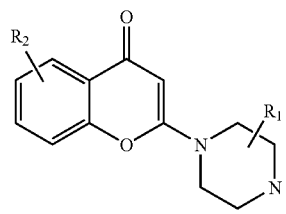

Formula A wherein the presence of each of $R_1$ and $R_2$ is optional and $R_1$ and $R_2$ are each independently selected from alkyl; substituted alkyl; heteroalkyl; cycloalkyl; substituted cycloalkyl; heterocycloalkyl; substituted heterocycloalky selected from piperazinyl, morpholinyl, tetrahydropyranyl, tetrahydrofuranyl, piperidinyl, pyrrolindinyl, or oxazolinyl, in which one or more hydrogen or carbon atom is replaced by another group selected from a halogen, aryl, substituted aryl, alkoxy, aryloxy, amino or a combination thereof; aryl selected from phenyl, naphthyl, biphenyl, diphenylether, diphenylamine or benzophenone; substituted aryl selected from phenyl, naphthyl, biphenyl, diphenylether, diphenylamine or benzophenone in which one or more hydrogen or carbon atom is replaced by one or more functional groups selected from alkyl, substituted alkyl, cycloalkyl, substituted cycloalkyl, heterocycloalkyl, substituted heterocycloalkyl, halogen, alkylhalos, hydroxy, amino, alkoxy, or thio; heteroaryl selected from thiophene, pyridine, isoxazole, phthalidimide, pyrazole, indole, or furan; substituted heteroaryl selected from thiophene, pyridine, isoxazole, phthalidimide, pyrazole, indole, or furan in which one or more hydrogen or carbon atom is replaced by one or more functional groups selected from alkyl, substituted alkyl, cycloalkyl, substituted cycloalkyl, heterocycloalkyl, substituted heterocycloalkyl, halogen, alkylhalo, hydroxy, amino, alkoxy, or thio; alkoxy; halogen; hydroxy; or amino, wherein the 2-(4-piperazinyl)-substituted 4H-1-benzopyran-4-one compound inhibits mammalian Target of Rapamycin or casein kinase 2, but does not significantly inhibit phosphatidylinositol 3-kinase.

2. The method of claim 1, wherein the 2-(4-piperazinyl)-substituted 4H-1-benzopyran-4-one compound comprises a 2-(4-piperazinyl)-8-phenyl-4H-1-benzopyran-4-one compound having the structure of

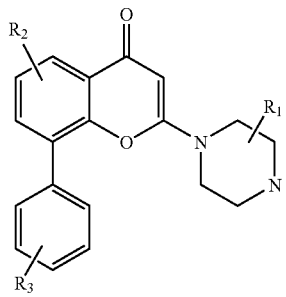

Formula B wherein the presence of each of $R_1$ and $R_2$ is optional and $R_1$ and $R_2$ are each independently selected from alkyl, aryl, alkoxy, halogen, hydroxy or amino, and wherein $R_3$ is not present.

3. The method of claim 1, wherein the 2-(4-piperazinyl)-substituted 4H-1-benzopyran-4-one compound comprises 2-(4-piperazinyl)-8-phenyl-4H-1-benzopyran-4-one.

4. The method of claim 1, further comprising contacting the cell with an effective amount of a chemotherapeutic agent.

5. The method of claim 1, wherein the cell is in vivo.

6. The method of claim 1, wherein the cell is in vitro.

7. A method of treating a proliferative disorder in a subject, comprising administering to the subject a therapeutically effective amount of a 2-(4-piperazinyl)-substituted 4H-1-benzopyran-4-one compound, or a pharmaceutically acceptable salt thereof, having the structure of

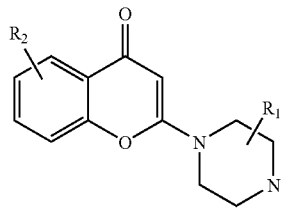

Formula A wherein the presence of each of $R_1$ and $R_2$ is optional and $R_1$ and $R_2$ are each independently selected from alkyl; substituted alkyl; heteroalkyl; cycloalkyl; substituted cycloalkyl; heterocycloalkyl; substituted heterocycloalkyl selected from piperazinyl, morpholinyl, tetrahydropyranyl, tetrahydrofuranyl, piperidinyl, pyrrolindinyl, or oxazolinyl, in which one or more hydrogen or carbon atom is replaced by another group selected from a halogen, aryl, substituted aryl, alkoxy, aryloxy, amino or a combination thereof; aryl selected from phenyl, naphthyl, biphenyl, diphenylether, diphenylamine or benzophenone; substituted aryl selected from phenyl, naphthyl, biphenyl, diphenylether, diphenylamine or benzophenone in which one or more hydrogen or carbon atom is replaced by one or more functional groups selected from alkyl, substituted alkyl, cycloalkyl, substituted cycloalkyl, heterocycloalkyl, substituted heterocycloalkyl, halogen, alkylhalo, hydroxy, amino, alkoxy, or thio; heteroaryl selected from thiophene, pyridine, isoxazole, phthalidimide, pyrazole, indole, or furan; substituted heteroaryl selected from thiophene, pyridine, isoxazole, phthalidimide, pyrazole, indole, or furan in which one or more hydrogen or carbon atom is replaced by one or more functional groups selected from alkyl, substituted alkyl, cycloalkyl, substituted cycloalkyl, heterocycloalkyl, substituted heterocycloalkyl, halogen, alkylhalo, hydroxy, amino, alkoxy, or thio; alkoxy; halogen; hydroxy; or amino, wherein the 2-(4-piperazinyl)-substituted 4H-1-benzopyran-4-one compound inhibits phosphorylation of P70 S6 kinase, but does not significantly inhibit phosphatidylinositol 3-kinase.

8. The method of claim 7, wherein the 2-(4-piperazinyl)-substituted 4H-1-benzopyran-4-one compound comprises a 2-(4-piperazinyl)-8-phenyl-4H-1-benzopyran-4-one compound having the structure of

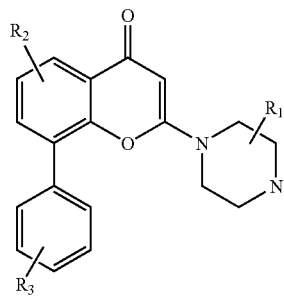

Formula B wherein the presence of each of $R_1$ and $R_2$ is optional and $R_1$ and $R_2$ are each independently selected from alkyl, aryl, alkoxy, halogen, hydroxy or amino, and wherein $R_3$ is not present.

9. The method of claim 7, wherein the 2-(4-piperazinyl)-substituted 4H-1-benzopyran-4-one compound comprises 2-(4-piperazinyl)-8-phenyl-4H-1-benzopyran-4-one.

10. The method of claim 7, wherein the proliferative disorder comprises restenosis.

11. The method of claim 10, wherein the 2-(4-piperazinyl)-substituted 4H-1-benzopyran-4-one compound is delivered in a vascular stent.

12. The method of claim 7, wherein the proliferative disorder is a tumor.

13. The method of claim 12, wherein the tumor is a lung cancer or a prostate cancer.

14. The method of claim 12, further comprising administering an additional chemotherapeutic agent to the subject.

15. The method of claim 14, wherein the chemotherapeutic agent is 5-fluorouracil (5-FU), azathioprine, cyclophosphamide, fludarabine, etoposide, doxorubicin, methotrexate, vincristine, carboplatin, cis-platinum, taxol, rapamycin, or a combination thereof.

16. The method of claim 12, wherein the tumor is a malignant tumor.

17. The method of claim 7, wherein the wherein the 2-(4-piperazinyl)-substituted 4H-1-benzopyran-4-one compound is delivered in a vascular stent.

\* \* \* \* \*